US012773103B2

(12) United States Patent
Feingold et al.

(10) Patent No.: US 12,773,103 B2
(45) Date of Patent: Oct. 27, 2026

(54) SYSTEMS AND METHODS FOR PROVIDING MEDICAL FLUORESCENCE IMAGING USING A ROLLING SHUTTER IMAGER AND A LIQUID CRYSTAL LIGHT SHUTTER

(71) Applicant: Stryker Corporation, Portage, MI (US)

(72) Inventors: Benjamin Hyman Feingold, San Francisco, CA (US); Chien Mien Pang, San Jose, CA (US); Levey Trac Tran, Denver, CO (US); Paul Roald Westwick, Vancouver (CA); Marc André, Spiegel b. Bern (CH)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/002,426

(22) Filed: Dec. 26, 2024

(65) Prior Publication Data

US 2025/0213101 A1 Jul. 3, 2025

Related U.S. Application Data

(60) Provisional application No. 63/615,748, filed on Dec. 28, 2023.

(51) Int. Cl.

*A61B 1/04* (2006.01)
*A61B 1/00* (2006.01)
*A61B 1/06* (2006.01)

(52) U.S. Cl.

CPC .......... *A61B 1/043* (2013.01); *A61B 1/00009* (2013.01); *A61B 1/046* (2022.02); *A61B 1/0638* (2013.01); *A61B 1/0684* (2013.01)

(58) Field of Classification Search

CPC ..... A61B 1/043; A61B 1/046; A61B 1/00009; A61B 1/0638; A61B 1/0684

See application file for complete search history.

(56) References Cited

U.S. PATENT DOCUMENTS

| | | | | |
|---|---|---|---|---|
| 5,944,748 A * | 8/1999 | Mager | A61N 5/0601 | |
| | | | 606/9 | |
| 10,368,752 B1 * | 8/2019 | Alford | A61B 5/0066 | |

(Continued)

FOREIGN PATENT DOCUMENTS

| | | | |
|---|---|---|---|
| JP | H10243936 A | 9/1998 | |
| WO | 2018/058013 A1 | 3/2018 | |

(Continued)

OTHER PUBLICATIONS

Extended European Search Report dated May 23, 2025, directed to EP Application No. 24223519.0; 9 pages.

(Continued)

*Primary Examiner* — Dixomara Vargas

(74) *Attorney, Agent, or Firm* — Morrison & Foerster LLP

(57) ABSTRACT

The present disclosure relates to techniques for imaging tissue of a subject. An exemplary method comprises transitioning a (liquid crystal) light shutter to an open state to allow reflected light from illuminating the tissue of the subject with a visible-light illumination source to accumulate charge at a plurality of rows of pixels of an imager; transitioning the light shutter to a closed state to prevent the imager from receiving visible light; during a first readout period, reading accumulated charge to produce a first set of imaging data; while the light shutter is in the closed state, illuminating the tissue of the subject with a fluorescence excitation illumination source; during a second readout period after the first readout period, reading accumulated charge to produce a second set of imaging data; and generating image frames based on the first set of imaging data and the second set of imaging data.

28 Claims, 16 Drawing Sheets

(56) References Cited

U.S. PATENT DOCUMENTS

| | | | | |
|---|---|---|---|---|
| 11,903,557 | B2 * | 2/2024 | Lord | A61B 5/7425 |
| 2002/0161282 | A1 * | 10/2002 | Fulghum | A61B 1/07 600/178 |
| 2010/0056928 | A1 * | 3/2010 | Zuzak | G01J 3/2823 356/302 |
| 2015/0025391 | A1 | 1/2015 | Mackie et al. | |
| 2015/0133751 | A1 * | 5/2015 | Stewart | A61B 5/1459 356/302 |
| 2015/0173715 | A1 * | 6/2015 | Raghavan | G16H 40/67 600/443 |
| 2016/0069807 | A1 | 3/2016 | Hatanaka et al. | |
| 2017/0035280 | A1 * | 2/2017 | Yang | A61B 1/0638 |
| 2018/0234603 | A1 | 8/2018 | Moore | |
| 2018/0288404 | A1 * | 10/2018 | Ikehara | A61B 5/743 |
| 2019/0029090 | A1 * | 1/2019 | Ikehara | G02B 21/16 |
| 2020/0234439 | A1 * | 7/2020 | Chang | A61B 5/0084 |
| 2022/0104693 | A1 * | 4/2022 | Baumann | A61B 1/043 |
| 2022/0210309 | A1 * | 6/2022 | Feingold | A61B 1/00009 |
| 2022/0273165 | A1 * | 9/2022 | Ouyang | A61B 1/0646 |
| 2022/0296090 | A1 * | 9/2022 | Ouyang | A61B 1/00103 |
| 2023/0421912 | A1 * | 12/2023 | Stead | G03B 9/02 |
| 2025/0311936 | A1 * | 10/2025 | Dunn | A61B 5/0042 |
| 2025/0387020 | A1 * | 12/2025 | Bauer | A61B 1/00186 |
| 2026/0000282 | A1 * | 1/2026 | Feingold | A61B 1/043 |

FOREIGN PATENT DOCUMENTS

| | | | |
|---|---|---|---|
| WO | 2022/147416 | A1 | 7/2022 |
| WO | 2024/011209 | A2 | 1/2024 |

OTHER PUBLICATIONS

International Search Report and Written Opinion mailed Sep. 18, 2025, directed to International Application No. PCT/US2025/035214; 12 pages.

* cited by examiner

ILLUMINATION SCHEME - EXAMPLE 2

ILLUMINATION SCHEME - EXAMPLE 3

SYSTEMS AND METHODS FOR PROVIDING MEDICAL FLUORESCENCE IMAGING USING A ROLLING SHUTTER IMAGER AND A LIQUID CRYSTAL LIGHT SHUTTER

CROSS-REFERENCE TO RELATED APPLICATION

This application claims the benefit of U.S. Provisional Application No. 63/615,748, filed on Dec. 28, 2023, the entire content of which is incorporated herein by reference for all purposes.

FIELD

The present disclosure relates generally to medical imaging, and more specifically to techniques for providing medical fluorescence imaging (e.g., open-field surgery fluorescence visualization) with a rolling shutter imager and a light shutter.

BACKGROUND

Medical systems, instruments or tools are utilized pre-surgery, during surgery, or post-operatively for various purposes. In particular, medical imaging systems can be used to enable a surgeon to view a surgical site in open-field procedures and endoscopic procedures. For example, endoscopy in the medical field allows internal features of the body of a patient to be viewed without the use of traditional, fully invasive surgery. Endoscopic imaging systems incorporate endoscopes to enable a surgeon to view a surgical site, and endoscopic tools enable non-invasive surgery at the site. Endoscopes may be usable along with a camera system for processing the images received by the endoscope. An endoscopic camera system typically includes a camera head connected to a camera control unit (CCU) that processes input image data received from the image sensor of the camera and outputs the image data for display. The CCU may control an illuminator that generates illumination light provided to the imaged scene.

Various image sensors may be used in imaging systems (e.g., endoscopic imaging systems, open-field imaging systems), including charge-coupled device (CCD) sensors and complementary metal oxide semiconductor (CMOS) sensors. The construction of CCDs is generally more complex than the construction of CMOS sensors, and CMOS sensors may be built in high volume wafer fabrication facilities used for related technologies such as microprocessors and chip sets. As a result, CMOS sensors are often less costly than CCDs for similar performance. In addition to lower cost, the common fabrication processes used to create CMOS imagers permits a CMOS pixel array to be integrated on a single circuit with other electronic devices such as clock drivers, digital logic, analog/digital converters, and other suitable electronics. The compact structures possible for a CMOS imager may also reduce space requirements and lower power consumption. CMOS imagers can also have higher sensitivity and provide higher video frame rates.

CMOS based imagers may utilize electronic rolling shutters to expose pixels in the sensor array. With an electronic rolling shutter, rows of pixels are cleared (or reset), exposed, and read out in sequence. During integration, a row of pixels is exposed to light energy and each pixel builds an electric charge corresponding to the amount and wavelengths of light impinging on the pixel. Because the rows are activated and read out in sequence, there is an elapsed time between when the first row integrates and when the last row integrates. Because of the elapsed time between when the first row begins to integrate and when the subsequent rows begin to integrate, a CMOS imager with an electronic rolling shutter may capture video images with blur or other rolling shutter effects. CMOS based imagers may also utilize global shutters to expose pixels in the sensor array. With a global shutter, all rows of pixels are exposed at the same time (i.e., same start and end of exposure) but the readout may be (and usually is) sequential.

Medical imaging systems (e.g., endoscopic imaging systems, open-field imaging systems) may include both a white-light illumination source and a fluorescence excitation illumination source. The white-light illumination source and the fluorescence excitation illumination source can be used to illuminate a tissue of a subject to obtain different types of image data (e.g., fluorescence image frames, white-light image frames, blended image frames). In particular, the fluorescence excitation illumination source, such as an infrared light illumination source, can provide illumination to the imaged tissue to excite the fluorophores (or fluorochromes) to produce fluorescence emission.

For medical imaging systems, rolling shutter imagers provide several advantages over global shutter imagers. For example, rolling shutter imagers can be more cost-effective, more robust, require lower power consumption, provide higher resolution and frame rates, and more compact and lightweight. However, rolling shutter images are currently not used for fluorescence visualization in open-field surgeries such as minimally invasive surgeries. This is because the ambient lighting (e.g., from the surgical room environment) can introduce significant contamination to fluorescence image frames for both global shutter and rolling shutter imagers, but may be especially challenging to address with rolling shutter imagers. Thus, techniques for enabling the use of rolling shutter imagers in open-field surgical imaging applications such as fluorescence visualization are desirable.

SUMMARY

Examples of the present disclosure include various examples of an illumination scheme that enables the use of imagers such as rolling shutter imagers and global shutter imagers in open-field surgical imaging applications such as fluorescence visualization. The techniques described herein can provide an improved medical imaging system because rolling shutter imagers provide several advantages over global shutter imagers. For example, rolling shutter imagers can be more cost-effective, more robust, require lower power consumption, more compact and lightweight, and can provide higher resolution and frame rates.

In particular, the techniques described herein can utilize a light shutter, such as a liquid crystal (LC) shutter, for selective blocking of visible light from reaching the imager, which can reduce the effect of ambient light on fluorescence imaging and can enable the use of rolling shutter imagers in open-field surgical imaging applications. The light shutter has an open state and a closed state and can transition between the two states based on a control signal for operating the light shutter, as described herein. In some examples, the light shutter is a liquid crystal (LC) shutter. The light shutter can behave differently for a light reflected from illumination of a tissue of the subject by the visible-light illumination source and a light emitted due to illumination of a tissue of the subject by the fluorescence excitation illumination source. Specifically, the light shutter can, in the open state, allow the passage of the light reflected from illumination of the tissue of the subject with the visible-light illumination such that the reflected light can reach the imager. In the closed state, the light shutter can prevent the light reflected from illumination of the tissue of the subject from reaching the imager or significantly attenuate the reflected light reaching the imager.

In contrast, regardless of which state the light shutter is in (e.g., the open state, the closed state, the transitioning state from the open state to the closed state, the transitioning state from the closed state to the open state), the light shutter can always allow the passage of a light emitted due to illumination of the tissue of the subject with the fluorescence excitation illumination source. In other words, the light shutter can transmit the fluorescence light emitted due to illumination of the tissue of the subject with the fluorescence excitation illumination even when the light shutter is in the closed state, so the opening and/or closing of the light shutter only affects the passage of the light reflected from illumination of the tissue of the subject with the visible-light illumination. When the light shutter is in the closed state, no light reflected from illumination of the tissue of the subject with the visible-light illumination source is transmitted; instead, only the light emitted due to illumination of the tissue of the subject with the fluorescence excitation illumination source is transmitted.

In some examples of an illumination scheme, an exemplary system with an imager (e.g., rolling shutter imager, global shutter imager) can transition the liquid crystal light shutter to the open state to allow reflected light from illumination of the tissue of the subject with the visible-light illumination source to accumulate charge at a plurality of rows of pixels of the imager. The system can then transition the liquid crystal light shutter to the closed state to prevent the imager from receiving visible light (including ambient visible light). During a first readout period, the system can sequentially read a first set of accumulated charge at the plurality of rows of pixels from a first row to a last row of the plurality of rows to produce a first set of imaging data. The system can illuminate the tissue of the subject with the fluorescence excitation illumination source while the liquid crystal light shutter is in the closed state. During a second readout period after the first readout period, the system can sequentially read a second set of accumulated charge from the first row to the last row of the plurality of rows of pixels to produce a second set of imaging data. The system can generate one or more image frames based on the first set of imaging data and the second set of imaging data. In some examples, the imager is a rolling shutter imager. In some examples, the imager is a global shutter imager. The system provides a more robust solution for optionally blocking visible light than use of a traditional mechanical shutter or moveable filter.

The illumination scheme provides a number of technical advantages. The light shutter is used to prevent any visible-light illumination, including any ambient visible-light illumination, from reaching the imager, thus reducing contamination and resulting in clearer fluorescence imaging data.

In some examples of the illumination scheme, an exemplary system with a rolling shutter imager transitions a light shutter to the open state to allow reflected light from illumination of a tissue of a subject with a primary visible-light illumination pulse of a pulsed visible-light illumination source to accumulate charge at a plurality of rows of pixels of the rolling shutter imager. The system then transitions the light shutter to the closed state to prevent the rolling shutter imager from receiving reflected light from one or more compensating visible-light illumination pulses of the pulsed visible-light illumination source after the primary visible-light illumination pulse of the pulsed visible-light illumination source. During a first readout period, the system sequentially reads a first set of accumulated charge at the plurality of rows of pixels from a first row to a last row of the plurality of rows to produce a first set of imaging data. The system can illuminate the tissue of the subject with the fluorescence excitation illumination source. During a second readout period after the first readout period, the system sequentially reads a second set of accumulated charge from the first row to the last row of the plurality of rows of pixels to produce a second set of imaging data. The system can then generate one or more image frames based on the first set of imaging data and the second set of imaging data.

Such an illumination scheme can provide additional advantages. The visible-light illumination source comprises primary visible-light illumination pulses for illuminating the tissue of the subject to generate imaging data, and one or more compensating visible-light illumination pulses between each two neighboring primary visible-light illumination pulses. Without the compensating visible-light illumination pulses, the primary visible-light illumination pulses alone can occur at a frequency (e.g., 60 Hz) low enough to generate a visual strobe effect, which can be uncomfortable for the user (e.g., a medical practitioner such as a surgeon) and thus compromise patient safety. By increasing the number and frequency of pulses via added compensating visible-light illumination pulses, the visible-light illumination source can appear to generate a more continuous light, which can increase the user's visual comfort.

The light shutter is configurable to switch between the open state and the closed state in a relatively short period of time comparing to the frame rate of the imaging system. In some examples, the time for the light shutter to transition from one state to the other state can be lower than 17 milliseconds. In some examples, the time for the light shutter to transition from one state to the other state can be lower than 10 milliseconds. Accordingly, the light shutter can be configured to close quickly after each primary visible-light illumination pulse to prevent the compensating visible-light illumination pulses from affecting the imaging data.

According to some examples of the illumination scheme (e.g., FIGS. 5A-5E), the fluorescence excitation illumination source is continuously active (i.e., in a continuous-wave mode) during an imaging session. The always-on configuration produces consistent fluorescence readings in all image frames, which can be useful for processing. For example, a fluorescence image frame can be subtracted from other image frames to extract a visible-light image frame with no fluorescence component.

According to some examples of the illumination scheme (e.g., FIGS. 6A-6C), the fluorescence excitation illumination source is configured to provide fluorescence excitation illumination pulses rather than constant illumination. In the always-on configuration, the fluorescence excitation strength may be excessively high and cause an intense fluorescence emission that in turn generates a strong fluorescence signal in the camera of the rolling shutter imager. The strong fluorescence signal generated by the emission may reduce the background white-light average luminance of an image frame that has a fluorescence component and contaminate the image frame. By pulsing the fluorescence excitation illumination source (e.g., at a 71% duty cycle), the fluorescence excitation strength can be reduced, thereby reducing the risk of contaminating image frames with overwhelming fluorescence signals. Although this has the same effect as running a constantly active fluorescence excitation illumination source at a lower current, an advantage of pulsing the fluorescence excitation illumination source is the removal of any wavelength dependence that certain fluorescence excitation illumination sources (e.g., laser diodes) can have with respect to instantaneous current.

According to some examples of the illumination scheme (e.g., FIGS. 7A-7D), the fluorescence excitation illumination source is configured to provide fluorescence excitation illumination pulses on half of the image frames. For example, the fluorescence excitation illumination pulses can be provided for only the fluorescence image frame. The examples in FIGS. 7A-B can be a more energy-efficient configuration for operating the fluorescence excitation illumination source because pulsing the fluorescence excitation illumination source only for fluorescence image frames means that all of the fluorescence excitation illumination is used for imaging. By pulsing the fluorescence excitation illumination source only for fluorescence image frames, the same image quality can be achieved with half of the optical energy, half of the tissue heating, and half of the photobleaching effect. Furthermore, not providing fluorescence excitation illumination during visible-light illumination frames eliminates the need to correct for fluorescence in those frames.

In some examples (e.g., FIGS. 8A-8E) of the illumination scheme, the illumination scheme involves a series of three-image rotations. Three sets of imaging data are acquired in each three-image rotation, and subsequently the next three-image rotation starts. Each three-image rotation results in a visible-light image frame corresponding to a first readout period, followed by a first fluorescence image frame corresponding to a second readout period, then followed by a second fluorescence image frame corresponding to a third readout period. The fluorescence excitation illumination source is on for the entire duration of the second readout period and is otherwise off during the three-image rotation. The two fluorescence frames can be summed to produce an image with equal corresponding fluorescence excitation illumination for every line.

The three-image rotation scheme of FIGS. 8A and 8B allows for more excitation power to be used on the first fluorescence image frame while remaining below the maximum instantaneous fluorescence exposure. Additionally, pulsing the fluorescence excitation illumination source on for only one of the two fluorescence image frame readout periods (i.e., only during the second readout period 803*b*) is energy-efficient because all or substantially all of the fluorescence excitation illumination is used for imaging. By pulsing the fluorescence excitation illumination source on for only one of the two fluorescence image frame readout periods, the same image quality can be achieved with less optical energy, less tissue heating, and less of the photobleaching effect than would be possible with pulsing the fluorescence excitation illumination source for both image frame readout periods. Furthermore, not providing fluorescence excitation illumination during visible-light illumination frames eliminates the need to correct for fluorescence in those frames.

In some examples (e.g., FIGS. 9A-9B) of the illumination scheme, the illumination scheme involves a series of four-image rotations. Four sets of imaging data are acquired in each four-image rotation, and subsequently the next four-image rotation starts. The acquired imaging data includes a visible-light image frame, followed by an ambient light image frame, then followed by a first fluorescence image frame, then followed by a second fluorescence image frame. The two fluorescence image frames can be summed in processing to produce an image with equal corresponding fluorescence excitation illumination for every line. The ambient light image frame can be subtracted from aggregated fluorescence frames in processing to correct for the effects of ambient light.

In some examples, a user can select among various examples of the illumination scheme for operating the visible-light illumination source, the fluorescence excitation illumination source, and/or the light shutter. In some examples, one particular exemplary illumination scheme can be set as a default for the imaging system.

BRIEF DESCRIPTION OF THE FIGURES

The invention will now be described, by way of example only, with reference to the accompanying drawings, in which.

DETAILED DESCRIPTION

Figure 1A:
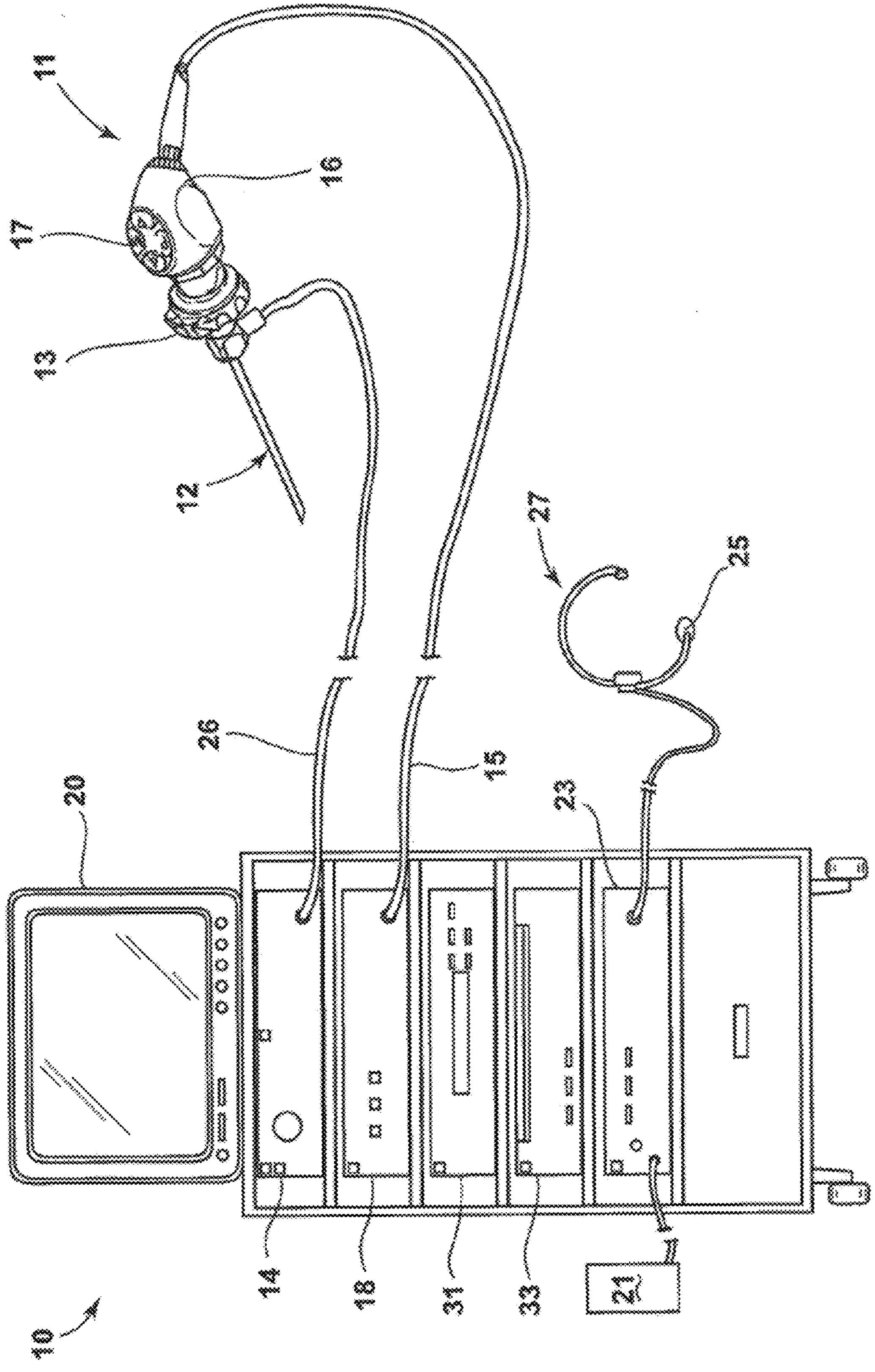
FIG. 1A is an illustration of an endoscopic camera system, according to some examples.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described. Examples will now be described more fully hereinafter with reference to the accompanying drawings; however, they may be embodied in different forms and should not be construed as limited to the examples set forth herein. Rather, these examples are provided so that this disclosure will be thorough and complete, and will fully convey exemplary implementations to those skilled in the art.

Examples of the present disclosure include various examples of an illumination scheme that enables the use of imagers such as rolling shutter imagers and global shutter imagers in open-field surgical imaging applications such as fluorescence visualization. The techniques described herein can provide an improved medical imaging system because rolling shutter imagers provide several advantages over global shutter imagers. For example, rolling shutter imagers can be more cost-effective, more robust, require lower power consumption, more compact and lightweight, and can provide higher resolution and frame rates.

In particular, the techniques described herein can utilize a light shutter, such as a liquid crystal (LC) shutter, for selective blocking of visible light from reaching the imager, which can reduce the effect of ambient light on fluorescence imaging and can enable the use of rolling shutter imagers in open-field surgical imaging applications. The light shutter has an open state and a closed state and can transition between the two states based on a control signal for operating the light shutter, as described herein. In some examples, the light shutter is a liquid crystal (LC) shutter. The light shutter can behave differently for a light reflected from illumination of a tissue of the subject by the visible-light illumination source and a light emitted due to illumination of a tissue of the subject by the fluorescence excitation illumination source. Specifically, the light shutter can, in the open state, allow the passage of the light reflected from illumination of the tissue of the subject with the visible-light illumination such that the reflected light can reach the imager. In the closed state, the light shutter can prevent the light reflected from illumination of the tissue of the subject from reaching the imager or significantly attenuate the reflected light reaching the imager.

In contrast, regardless of which state the light shutter is in (e.g., the open state, the closed state, the transitioning state from the open state to the closed state, the transitioning state from the closed state to the open state), the light shutter can always allow the passage of a light emitted due to illumination of the tissue of the subject with the fluorescence excitation illumination source. In other words, the light shutter can transmit the fluorescence light emitted due to illumination of the tissue of the subject with the fluorescence excitation illumination even when the light shutter is in the closed state, so the opening and/or closing of the light shutter only affects the passage of the light reflected from illumination of the tissue of the subject with the visible-light illumination. When the light shutter is in the closed state, no light reflected from illumination of the tissue of the subject with the visible-light illumination source is transmitted; instead, only the light emitted due to illumination of the tissue of the subject with the fluorescence excitation illumination source is transmitted.

In some examples of an illumination scheme, an exemplary system with an imager (e.g., rolling shutter imager, global shutter imager) can transition the liquid crystal light shutter to the open state to allow reflected light from illumination of the tissue of the subject with the visible-light illumination source to accumulate charge at a plurality of rows of pixels of the imager. The system can then transition the liquid crystal light shutter to the closed state to prevent the imager from receiving visible light (including ambient visible light). During a first readout period, the system can sequentially read a first set of accumulated charge at the plurality of rows of pixels from a first row to a last row of the plurality of rows to produce a first set of imaging data. The system can illuminate the tissue of the subject with the fluorescence excitation illumination source while the liquid crystal light shutter is in the closed state. During a second readout period after the first readout period, the system can sequentially read a second set of accumulated charge from the first row to the last row of the plurality of rows of pixels to produce a second set of imaging data. The system can generate one or more image frames based on the first set of imaging data and the second set of imaging data. In some examples, the imager is a rolling shutter imager. In some examples, the imager is a global shutter imager. The system provides a more robust solution for optionally blocking visible light than use of a traditional mechanical shutter or moveable filter.

The illumination scheme provides a number of technical advantages. The light shutter is used to prevent any visible-light illumination, including any ambient visible-light illumination, from reaching the imager, thus reducing contamination and resulting in clearer fluorescence imaging data.

In some examples of the illumination scheme, an exemplary system with a rolling shutter imager transitions a light shutter to the open state to allow reflected light from illumination of a tissue of a subject with a primary visible-light illumination pulse of a pulsed visible-light illumination source to accumulate charge at a plurality of rows of pixels of the rolling shutter imager. The system then transitions the light shutter to the closed state to prevent the rolling shutter imager from receiving reflected light from one or more compensating visible-light illumination pulses of the pulsed visible-light illumination source after the primary visible-light illumination pulse of the pulsed visible-light illumination source. During a first readout period, the system sequentially reads a first set of accumulated charge at the plurality of rows of pixels from a first row to a last row of the plurality of rows to produce a first set of imaging data. The system can illuminate the tissue of the subject with the fluorescence excitation illumination source. During a second readout period after the first readout period, the system sequentially reads a second set of accumulated charge from the first row to the last row of the plurality of rows of pixels to produce a second set of imaging data. The system can then generate one or more image frames based on the first set of imaging data and the second set of imaging data.

Such an illumination scheme can provide additional advantages. The visible-light illumination source comprises primary visible-light illumination pulses for illuminating the tissue of the subject to generate imaging data, and one or more compensating visible-light illumination pulses between each two neighboring primary visible-light illumination pulses. Without the compensating visible-light illumination pulses, the primary visible-light illumination pulses alone can occur at a frequency (e.g., 60 Hz) low enough to generate a visual strobe effect, which can be uncomfortable for the user (e.g., a medical practitioner such as a surgeon) and thus compromise patient safety. By increasing the number and frequency of pulses via added compensating visible-light illumination pulses, the visible-light illumination source can appear to generate a more continuous light, which can increase the user's visual comfort.

The light shutter is configurable to switch between the open state and the closed state in a relatively short period of time comparing to the frame rate of the imaging system. In some examples, the time for the light shutter to transition from one state to the other state can be lower than 17 milliseconds. In some examples, the time for the light shutter to transition from one state to the other state can be lower than 10 milliseconds. Accordingly, the light shutter can be configured to close quickly after each primary visible-light illumination pulse to prevent the compensating visible-light illumination pulses from affecting the imaging data.

According to some examples of the illumination scheme (e.g., FIGS. 5A-5E), the fluorescence excitation illumination source is continuously active (i.e., in a continuous-wave mode) during an imaging session. The always-on configuration produces consistent fluorescence readings in all image frames, which can be useful for processing. For example, a fluorescence image frame can be subtracted from other image frames to extract a visible-light image frame with no fluorescence component.

According to some examples of the illumination scheme (e.g., FIGS. 6A-6C), the fluorescence excitation illumination source is configured to provide fluorescence excitation illumination pulses rather than constant illumination. In the always-on configuration, the fluorescence excitation strength may be excessively high and cause an intense fluorescence emission that in turn generates a strong fluorescence signal in the camera of the rolling shutter imager. The strong fluorescence signal generated by the emission may reduce the background white-light average luminance of an image frame that has a fluorescence component and contaminate the image frame. By pulsing the fluorescence excitation illumination source (e.g., at a 71% duty cycle), the fluorescence excitation strength can be reduced, thereby reducing the risk of contaminating image frames with overwhelming fluorescence signals. Although this has the same effect as running a constantly active fluorescence excitation illumination source at a lower current, an advantage of pulsing the fluorescence excitation illumination source is the removal of any wavelength dependence that certain fluorescence excitation illumination sources (e.g., laser diodes) can have with respect to instantaneous current.

According to some examples of the illumination scheme (e.g., FIGS. 7A-7D), the fluorescence excitation illumination source is configured to provide fluorescence excitation illumination pulses on half of the image frames. For example, the fluorescence excitation illumination pulses can be provided for only the fluorescence image frame. The examples in FIGS. 7A-B can be a more energy-efficient configuration for operating the fluorescence excitation illumination source because pulsing the fluorescence excitation illumination source only for fluorescence image frames means that all of the fluorescence excitation illumination is used for imaging. By pulsing the fluorescence excitation illumination source only for fluorescence image frames, the same image quality can be achieved with half of the optical energy, half of the tissue heating, and half of the photobleaching effect. Furthermore, not providing fluorescence excitation illumination during visible-light illumination frames eliminates the need to correct for fluorescence in those frames.

In some examples (e.g., FIGS. 8A-8E) of the illumination scheme, the illumination scheme involves a series of three-image rotations. Three sets of imaging data are acquired in each three-image rotation, and subsequently the next three-image rotation starts. Each three-image rotation results in a visible-light image frame corresponding to a first readout period, followed by a first fluorescence image frame corresponding to a second readout period, then followed by a second fluorescence image frame corresponding to a third readout period. The fluorescence excitation illumination source is on for the entire duration of the second readout period and is otherwise off during the three-image rotation. The two fluorescence frames can be summed to produce an image with equal corresponding fluorescence excitation illumination for every line.

The three-image rotation scheme of FIGS. 8A and 8B allows for more excitation power to be used on the first fluorescence image frame while remaining below the maximum instantaneous fluorescence exposure. Additionally, pulsing the fluorescence excitation illumination source on for only one of the two fluorescence image frame readout periods (i.e., only during the second readout period 803*b*) is energy-efficient because all or substantially all of the fluorescence excitation illumination is used for imaging. By pulsing the fluorescence excitation illumination source on for only one of the two fluorescence image frame readout periods, the same image quality can be achieved with less optical energy, less tissue heating, and less of the photobleaching effect than would be possible with pulsing the fluorescence excitation illumination source for both image frame readout periods. Furthermore, not providing fluorescence excitation illumination during visible-light illumination frames eliminates the need to correct for fluorescence in those frames.

In some examples (e.g., FIGS. 9A-9B) of the illumination scheme, the illumination scheme involves a series of four-image rotations. Four sets of imaging data are acquired in each four-image rotation, and subsequently the next four-image rotation starts. The acquired imaging data includes a visible-light image frame, followed by an ambient light image frame, then followed by a first fluorescence image frame, then followed by a second fluorescence image frame. The two fluorescence image frames can be summed in processing to produce an image with equal corresponding fluorescence excitation illumination for every line. The ambient light image frame can be subtracted from aggregated fluorescence frames in processing to correct for the effects of ambient light.

In some examples, a user can select among various examples of the illumination scheme for operating the visible-light illumination source, the fluorescence excitation illumination source, and/or the light shutter. In some examples, one particular exemplary illumination scheme can be set as a default for the imaging system.

Accordingly, described herein are exemplary devices, apparatuses, systems, methods, and non-transitory storage media for medical imaging. More generally are described exemplary devices, systems, and methods for modulating a fluorescence excitation illumination source. The systems, devices, and methods may be used for imaging tissue of a subject, such as in endoscopic imaging procedures and in open-field surgical procedures. Imaging may be performed pre-operatively, intra-operatively, post-operatively, and during diagnostic imaging sessions and procedures. Further, the techniques can be applied in non-surgical or non-medical uses.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

Figure 1B:
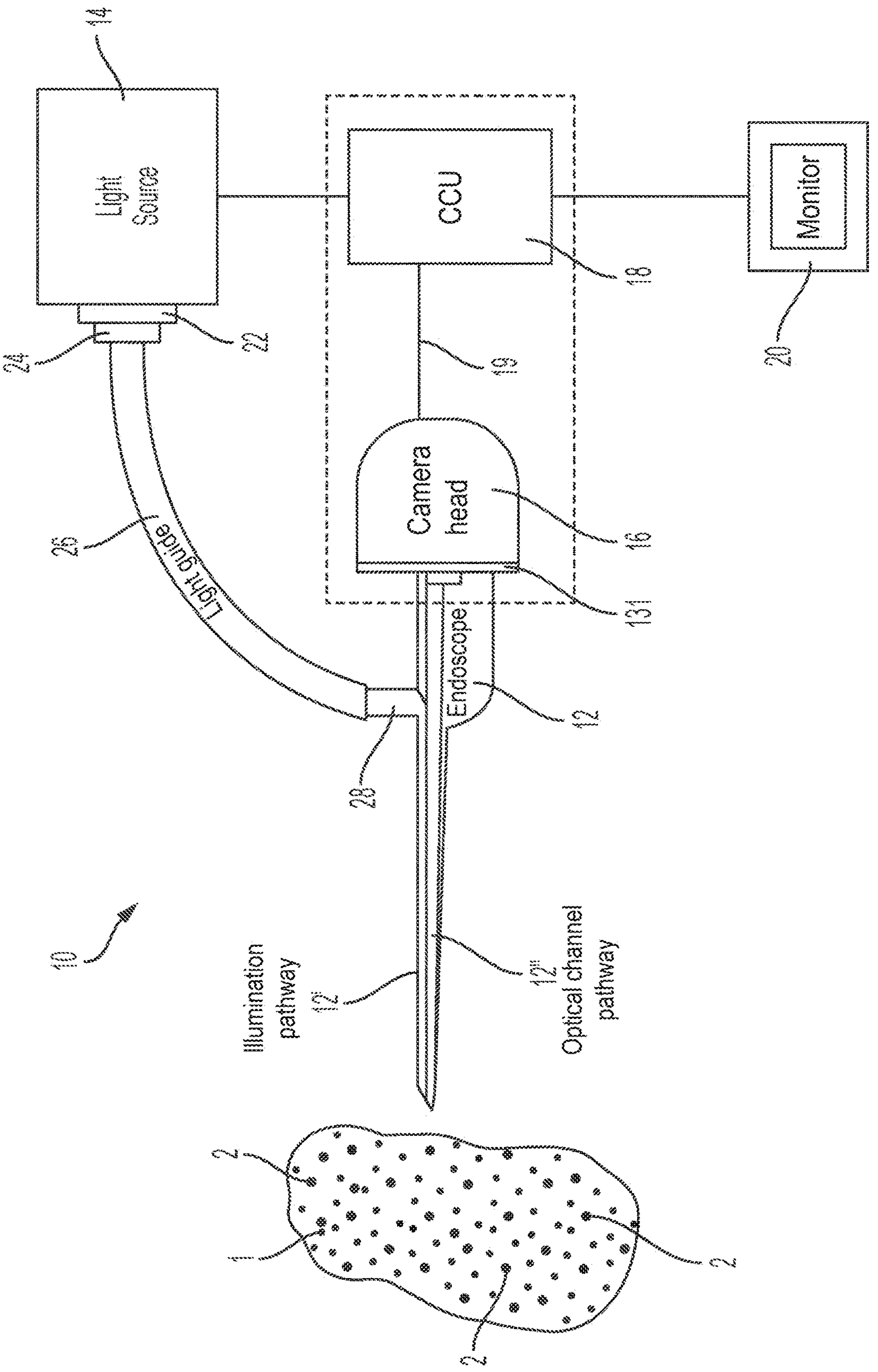
FIG. 1B is a diagram of a portion of the endoscopic camera system of FIG. 1A and a target object for imaging, according to some examples.
Figure 2A:
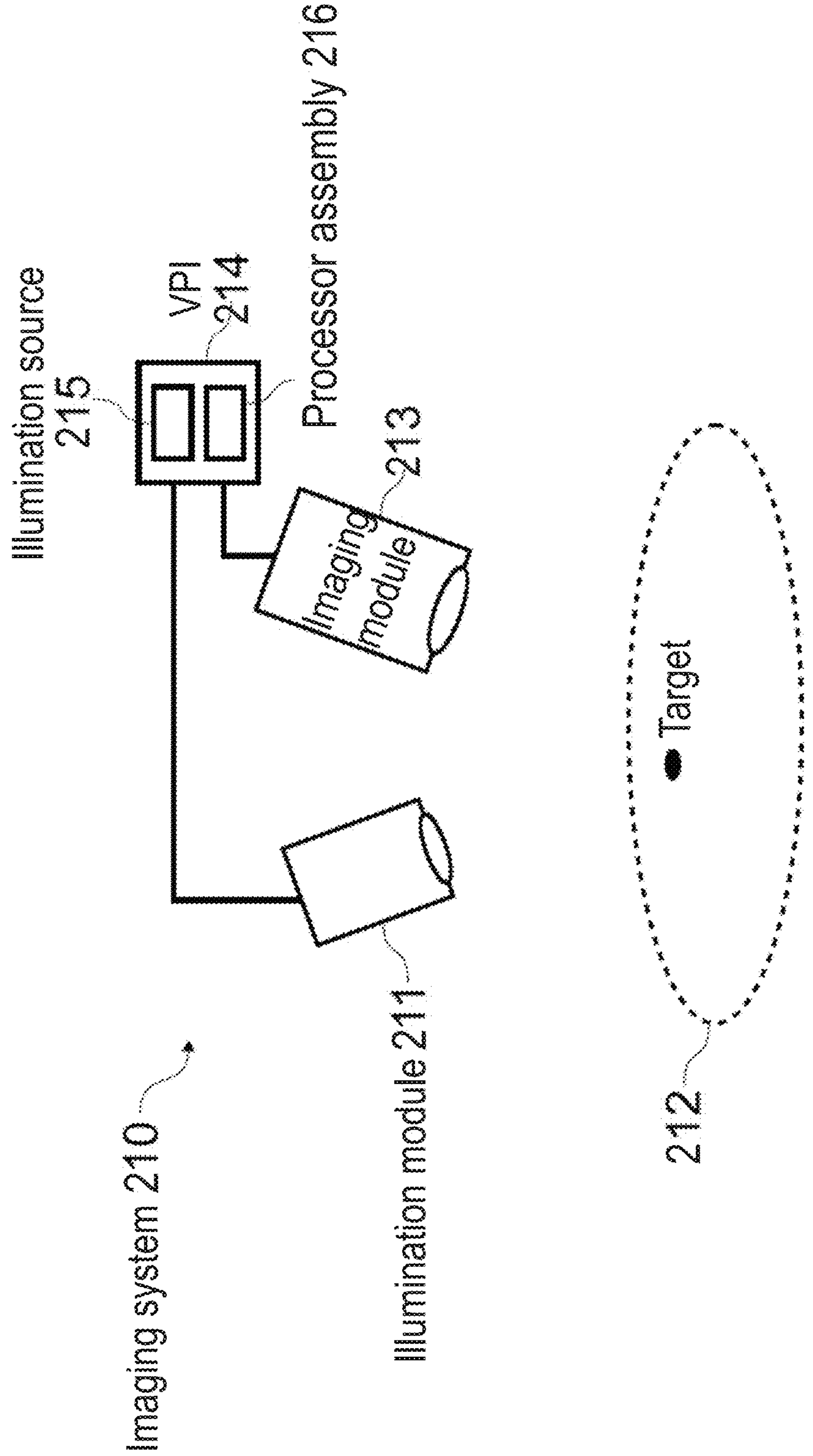
FIG. 2A illustrates a schematic view of a system for illumination and imaging in open-field surgeries, according to some examples.

Embodiments of the present disclosure may be incorporated into any medical imaging systems, including imaging systems used in minimally invasive surgeries (e.g., FIGS. 1A-B) and open field imaging systems (e.g., FIG. 2A). FIG. 1A shows an example of an endoscopic imaging system 10, which includes a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is connected to, and communicates with, the light source 14. Operation of the camera 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switching from one imaging mode to another, as discussed further below. Voice commands may be input into a microphone 25 mounted on a headset 27 worn by the practitioner and coupled to the voice-control unit 23. A hand-held control device 29, such as a tablet with a touch screen user interface or a PDA, may be coupled to the voice control unit 23 as a further control interface. In the illustrated example, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

FIG. 1B shows an example of a portion of the endoscopic system 10 being used to illuminate and receive light from an object 1, such as a surgical site of a patient. The object 1 may include fluorescent markers 2, for example, as a result of the patient being administered a fluorescence imaging agent. The fluorescent markers 2 may comprise, for example, indocyanine green (ICG).

The light source 14 can generate visible illumination light (such as any combination of red, green, and blue light) for generating visible (e.g., white light) images of the target object 1 and, in some examples, can also produce fluorescence excitation illumination light for exciting the fluorescent markers 2 in the target object for generating fluorescence images. In some examples, the light source 14 can produce fluorescence excitation illumination light for exciting autofluorescence in the target object for generating fluorescence images, additionally or alternatively to light for exciting the fluorescent markers. Illumination light is transmitted to and through an optic lens system 22 which focuses light onto a light pipe 24. The light pipe 24 may create a homogeneous light, which is then transmitted to the fiber optic light guide 26. The light guide 26 may include multiple optic fibers and is connected to a light post 28, which is part of the endoscope 12. The endoscope 12 includes an illumination pathway 12' and an optical channel pathway 12".

The endoscope 12 may include a notch filter 131 that allows some or all (preferably, at least 80%) of fluorescence emission light (e.g., in a wavelength range of 830 nm to 870 nm) emitted by fluorescence markers 2 in the target object 1 to pass therethrough and that allows some or all (preferably, at least 80%) of visible light (e.g., in the wavelength range of 400 nm to 700 nm), such as visible illumination light reflected by the target object 1, to pass therethrough, but that blocks substantially all of the fluorescence excitation light (e.g., infrared light having a wavelength of 780 nm, 808 nm, or the like) that is used to excite fluorescence emission from the fluorescent marker 2 in the target object 1. The notch filter 131 may have an optical density of OD5 or higher. In some examples, the notch filter 131 can be located in the coupler 13.

FIG. 2A illustrates an exemplary open field imaging system in accordance with some examples. FIG. 2A illustrates a schematic view of an illumination and imaging system 210 that can be used in open field surgical procedures. As may be seen therein, the system 210 may include an illumination module 211, an imaging module 213, and a video processor/illuminator (VPI) 214. The VPI 214 may include an illumination source 215 to provide illumination to the illumination module 211 and a processor assembly 216 to send control signals and to receive data about light detected by the imaging module 213 from a target 212 illuminated by light output by the illumination module 211. In one variation, the video processor/illuminator 214 may comprise a separately housed illumination source 215 and the processor assembly 216. In one variation, the video processor/illuminator 214 may comprise the processor assembly 216 while one or more illumination sources 215 are separately contained within the housing of the illumination module 211. The illumination source 215 may output light at different waveband regions, e.g., white (RGB) light, excitation light to induce fluorescence in the target 212, a combination thereof, and so forth, depending on characteristics to be examined and the material of the target 212. Light at different wavebands may be output by the illumination source 215 simultaneously, sequentially, or both. The illumination and imaging system 210 may be used, for example, to facilitate medical (e.g., surgical) decision-making, e.g., during a surgical procedure. The target 212 may include fluorescent markers, for example, as a result of the patient being administered a fluorescence imaging agent. The fluorescent markers may comprise, for example, indocyanine green (ICG). The target 212 may be a topographically complex target, e.g., a biological material including tissue, an anatomical structure, other objects with contours and shapes resulting in shadowing when illuminated, and so forth. The VPI 214 may record, process, display, and so forth, the resulting images and associated information.

Figure 2B:
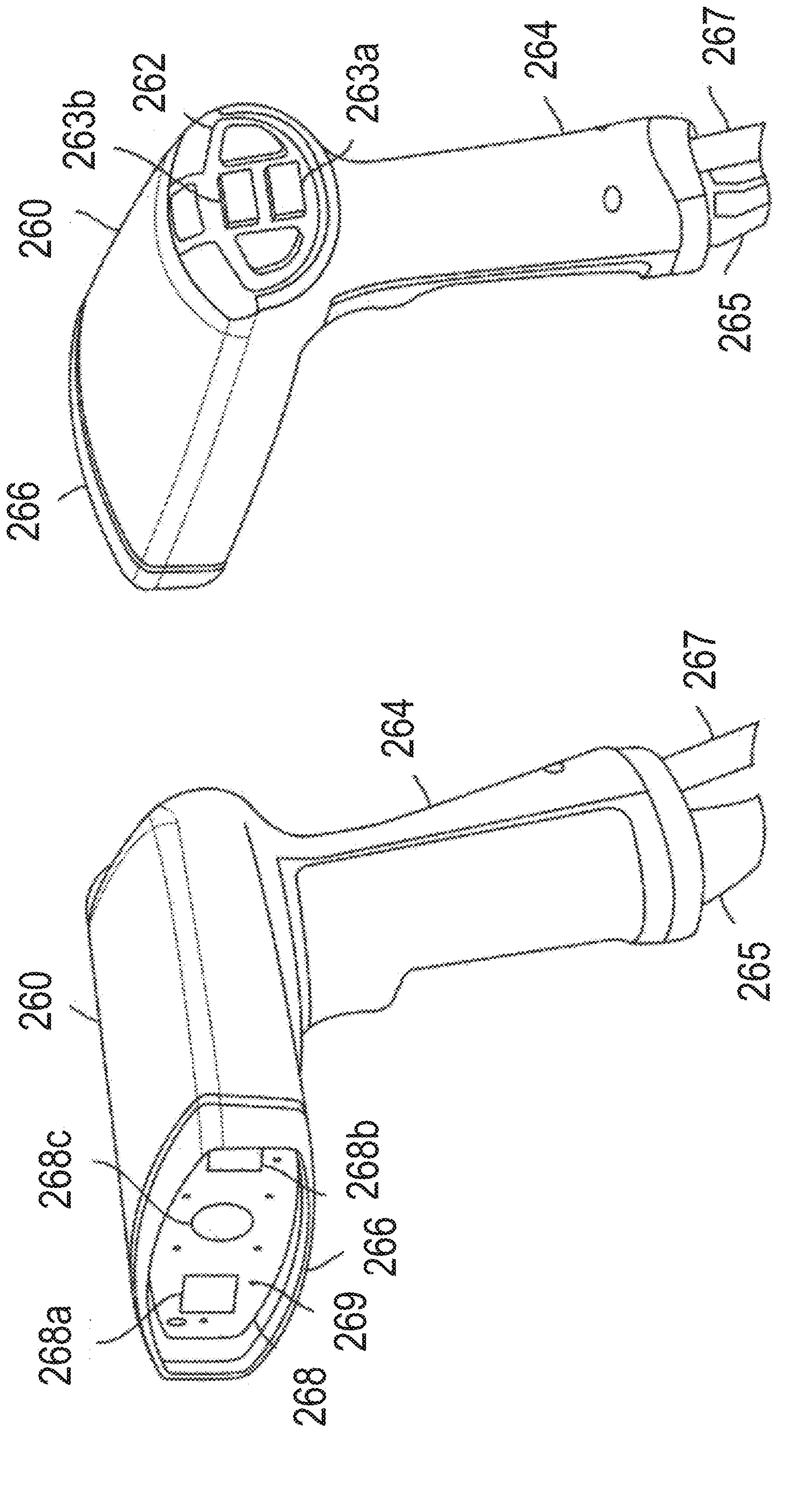
FIG. 2B illustrates another exemplary system for illumination and imaging in open-field surgeries, according to some examples.

FIG. 2B illustrates an additional example of an open field surgical imaging system or a portion thereof. With reference to FIG. 2B, an ergonomic enclosure 260 can be designed to be held in a pistol-style grip. The enclosure 260 may include a control surface 262, a grip 264, a window frame 268 and a nosepiece 266. The ergonomic enclosure is connectable to a VPI box (not depicted) via a light guide cable 267, through which the light is provided to one or more illumination ports (not depicted), and a data cable 265 that transmits power, sensor data, and any other (non-light) connections.

The control surface 262 includes focus buttons **263*a* and 263*b* that control the focus actuation assembly. Other buttons on the control surface 262** may be programmable and may be used for various other functions, excitation laser power on/off, display mode selection, white light imaging white balance, saving a screenshot, and so forth. Alternatively or additionally to the focus buttons, a proximity sensor may be provided on the enclosure and may be employed to automatically adjust the focus actuation assembly.

Enclosure 260 may be operated by a single hand in a pistol-grip style orientation. In various other examples, the enclosure 260 may be supported on a support (e.g., a movable support). In some examples, enclosure 260 may be used in concert with a drape. Window frame 268 may include windows **268*a* and 268*b*, corresponding to two lens modules, as well as window 268*c*, which serves as an input window for light from the target to be incident on the image sensor. Window frame 268 may also include one or more windows 269** for sensors provided behind a plate.

Figure 3:
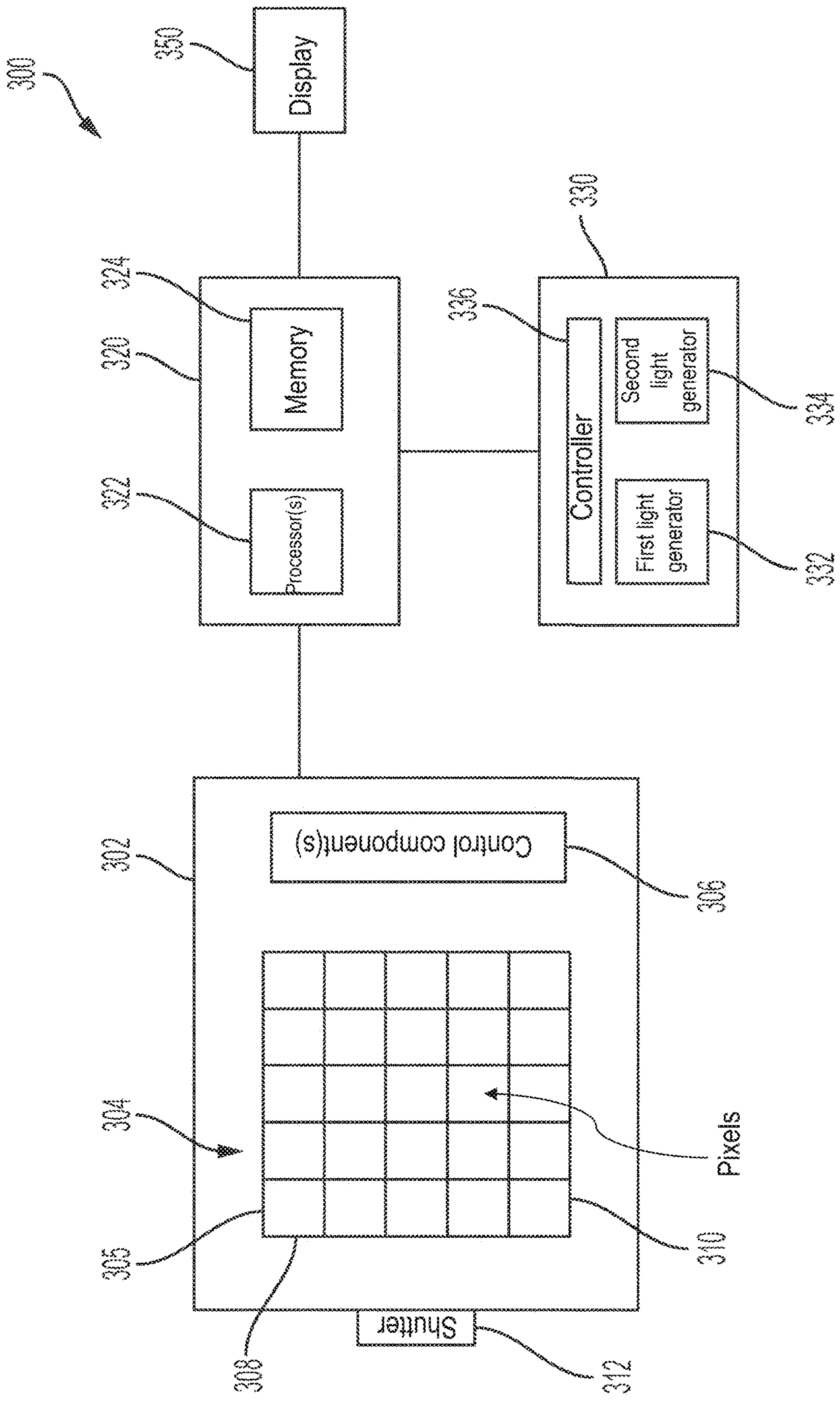
FIG. 3 is a block diagram of an imaging system, according to some examples.

FIG. 3 schematically illustrates an exemplary imaging system 300 that employs an electronic imager 302 to generate images (e.g., still and/or video) of a target object, such as a target tissue of a patient, according to some examples. The imager 302 may be a rolling shutter imager (e.g., CMOS sensors) or a global shutter imager (e.g., CCD sensors, CMOS sensors). System 300 may be used, for example, for the endoscopic imaging system 10 of FIG. 1A. The imager 302 includes a CMOS sensor 304 having an array of pixels 305 arranged in rows of pixels 308 and columns of pixels 310. The imager 302 may include control components 306 that control the signals generated by the CMOS sensor 304. Examples of control components include gain circuitry for generating a multi-bit signal indicative of light incident on each pixel of the sensor 304, one or more analog-to-digital converters, one or more line drivers to act as a buffer and provide driving power for the sensor 304, row circuitry, and timing circuitry. A timing circuit may include components such as a bias circuit, a clock/timing generation circuit, and/or an oscillator. Row circuitry may enable one or more processing and/or operational tasks such as addressing rows of pixels 308, addressing columns of pixels 310, resetting charge on rows of pixels 308, enabling exposure of pixels 305, decoding signals, amplifying signals, analog-to-digital signal conversion, applying timing, readout, and reset signals, and other suitable processes or tasks. Imager 302 may also include a shutter 312 that may be used, for example, to control exposure of the image sensor 304 and/or to control an amount of light received at the image sensor 304.

One or more control components may be integrated into the same integrated circuit in which the sensor 304 is integrated or may be discrete components. The imager 302 may be incorporated into an imaging head, such as camera head 16 of system 10.

One or more control components 306, such as row circuitry and a timing circuit, may be electrically connected to an imaging controller 320, such as camera control unit 18 of system 10. The imaging controller 320 may include one or more processors 322 and memory 324. The imaging controller 320 receives imager row readouts and may control readout timings and other imager operations, including mechanical shutter operation. The imaging controller 320 may generate image frames, such as video frames from the row and/or column readouts from the imager 302. Generated frames may be provided to a display 350 for display to a user, such as a surgeon.

The system 300 in this example includes a light source 330 for illuminating a target scene. The light source 330 is controlled by the imaging controller 320. The imaging controller 320 may determine the type of illumination provided by the light source 330 (e.g., white light, fluorescence excitation light, or both), the intensity of the illumination provided by the light source 330, and or the on/off times of illumination in synchronization with image sensor shutter operation. The light source 330 may include a first light generator 332 for generating light in a first wavelength and a second light generator 334 for generating light in a second wavelength. In some examples, the first light generator 332 is a white light generator, which may be comprised of multiple discrete light generation components (e.g., multiple LEDs of different colors), and the second light generator 334 is a fluorescence excitation light generator, such as a laser diode.

The light source 330 includes a controller 336 for controlling light output of the light generators. The controller 336 may be configured to provide pulse width modulation (PWM) of the light generators for modulating intensity of light provided by the light source 330, which can be used to manage overexposure and underexposure. In some examples, nominal current and/or voltage of each light generator remains constant, and the light intensity is modulated by switching the light generators (e.g., LEDs) on and off according to a PWM control signal. In some examples, a PWM control signal is provided by the imaging controller 336. This control signal can be a waveform that corresponds to the desired pulse width modulated operation of light generators.

The imaging controller 320 may be configured to determine the illumination intensity required of the light source 330 and may generate a PWM signal that is communicated to the light source 330. In some examples, depending on the amount of light received at the sensor 304 and the integration times, the light source may be pulsed at different rates to alter the intensity of illumination light at the target scene. The imaging controller 320 may determine a required illumination light intensity for a subsequent frame based on an amount of light received at the sensor 304 in a current frame and/or one or more previous frames. In some examples, the imaging controller 320 is capable of controlling pixel intensities via PWM of the light source 330 (to increase/decrease the amount of light at the pixels), via operation of the shutter 312 (to increase/decrease the amount of light at the pixels), and/or via changes in gain (to increase/decrease sensitivity of the pixels to received light). In some examples, the imaging controller 320 primarily uses PWM of the illumination source for controlling pixel intensities while holding the shutter open (or at least not operating the shutter) and maintaining gain levels. The controller 320 may operate the shutter 312 and/or modify the gain in the event that the light intensity is at a maximum or minimum and further adjustment is needed.

Figure 4:
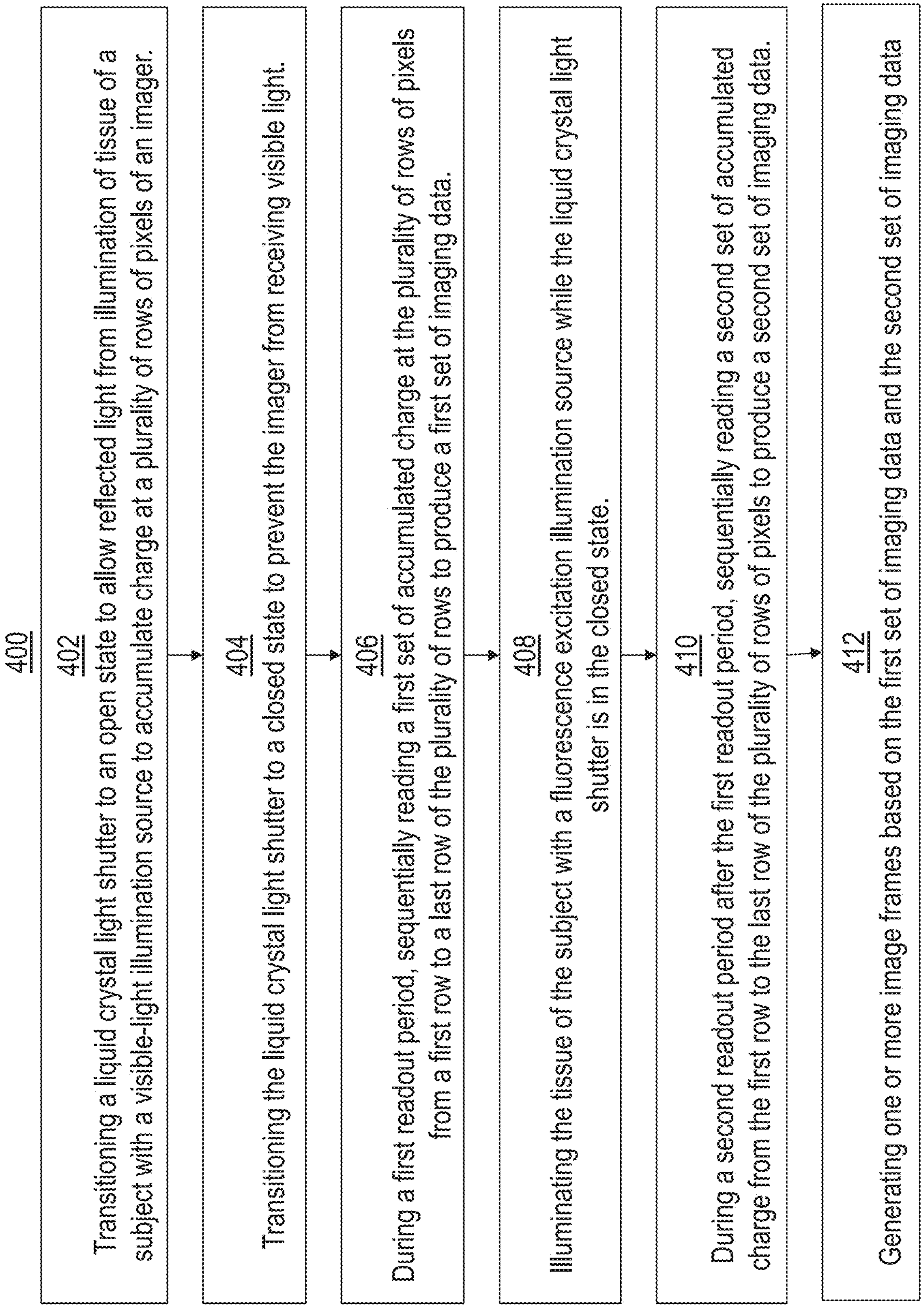
FIG. 4 provides an exemplary method for imaging tissue of a subject, in accordance with some examples.

FIG. 4 provides an exemplary method 400 for imaging tissue of a subject, in accordance with some examples. Method 400 may be performed by an imaging system that comprises an imager (e.g., a rolling shutter imager, a global shutter imager), a liquid crystal light shutter configurable to be in an open state and a closed state, a fluorescence excitation illumination source, and a visible-light illumination source. In some examples, the fluorescence excitation illumination source comprises an infrared light. In some examples, the visible-light illumination source comprises one or more LEDs. In some examples, the imager is part of an endoscopic imager or an open-field imager and may comprise a CMOS sensor. In some examples, the imaging system is the imaging system 300 of FIG. 3, which has an imager (e.g., rolling shutter imager 302 of system 300) and a light source (e.g., light source 330 of system 300) that can comprise a fluorescence excitation illumination source and/or a visible-light illumination source.

In process 400, some blocks are optionally combined, the order of some blocks is optionally changed, and some blocks are optionally omitted. In some examples, additional steps may be performed in combination with the process 400. Accordingly, the operations as illustrated (and described in greater detail below) are exemplary by nature and, as such, should not be viewed as limiting.

At block 402, an exemplary system transitions the light shutter to the open state to allow reflected light from illumination of the tissue of the subject with the visible-light illumination source to accumulate charge at a plurality of rows of pixels of the imager. At block 404, the system transitions the light shutter to the closed state to prevent the imager from receiving visible light. At block 406, during a first readout period, the system sequentially reads a first set of accumulated charge at the plurality of rows of pixels from a first row to a last row of the plurality of rows to produce a first set of imaging data. At block 408, the system illuminates the tissue of the subject with the fluorescence excitation illumination source while the light shutter is in the closed state. At block 410, during a second readout period after the first readout period, the system sequentially reads a second set of accumulated charge from the first row to the last row of the plurality of rows of pixels to produce a second set of imaging data. At block 412, the system generates one or more image frames based on the first set of imaging data and the second set of imaging data.

In some examples, transitioning the light shutter to the closed state to prevent the imager from receiving visible light comprises transitioning the light shutter to the closed state to prevent the imager from receiving ambient light.

In some examples, the imager is a rolling shutter imager, and the visible-light illumination source is pulsed. In some examples, the system may illuminate the tissue of the subject with a primary visible-light illumination pulse of the pulsed visible-light illumination source while the light shutter is in the open state. In some examples, the system may illuminate the tissue of the subject with one or more compensating visible-light illumination pulses of the pulsed visible-light illumination source after the primary visible-light illumination pulse of the pulsed visible-light illumination source and while the light shutter is in the closed state.

In some examples, the one or more image frames comprise a visible-light image frame based on the first set of imaging data and wherein the one or more image frames comprise a fluorescence image frame based on the second set of imaging data. In some examples, the one or more image frames comprise a blended image frame based on the fluorescence image frame and the visible-light image frame. In some examples, the fluorescence image frame is overlaid on the visible-light image frame in the blended image frame. The blended image frame is derived from colorizing the visible-light image frame based on the fluorescence image frame (e.g., colorizing the visible-light image frame based on the ratio of the fluorescence image frame to one or more channels of the visible-light frame). In some examples, the method further comprises adding the one or more image frames to a video stream.

In some examples, the primary visible-light illumination pulse is a first primary visible-light illumination pulse. During the second readout period, the system transitions the light shutter to the open state to allow illumination of the tissue of the subject with a second primary visible-light illumination pulse of the pulsed visible-light illumination source to accumulate charge at the plurality of rows of pixels of the rolling shutter imager. The second primary visible-light illumination pulse is immediately after the one or more compensating visible-light illumination pulses.

In some examples, the first readout period and the second readout period form an image acquisition rotation. The system can perform one or more additional image acquisition rotations.

In some examples, the fluorescence excitation illumination source is continuously on during the image acquisition rotation.

In some examples, the fluorescence excitation illumination source is pulsed to reduce fluorescence intensity in the second set of imaging data.

In some examples, the fluorescence excitation illumination source is pulsed, and the fluorescence excitation illumination source is configured to output a single fluorescence excitation illumination pulse during the image acquisition rotation to illuminate the tissue of the subject.

In some examples, the fluorescence excitation illumination source is pulsed. During a third readout period after the second readout period, the system sequentially reads a third set of accumulated charge at the plurality of rows of pixels from the first row to the last row of the plurality of rows to produce a third set of imaging data, the pulsed fluorescence excitation illumination source is configured to output a single pulse spanning the second readout period during the first readout period, the second readout period, and the third readout period. In some examples, the first readout period, the second readout period, and the third readout period form an image acquisition rotation, and the system can perform one or more additional image acquisition rotations. In some examples, the one or more image frames comprise a visible-light image frame based on the first set of imaging data and wherein the one or more image frames comprise a fluorescence image frame based on the second set of imaging data and the third set of imaging data.

In some examples, the system adds an ambient readout period between the first readout period and the second readout period. During the ambient readout period, the system sequentially reads a fourth set of accumulated charge at the plurality of rows of pixels from the first row to the last row of the plurality of rows to produce a set of ambient imaging data. In some examples, the first readout period, the ambient readout period, the second readout period, and the third readout period form an image acquisition rotation, and the system can perform one or more additional image acquisition rotations. In some examples, the one or more image frames comprise a visible-light image frame based on the first set of imaging data and the one or more image frames comprise a fluorescence image frame based on the second set of imaging data, the third set of imaging data, and the set of ambient imaging data.

In some examples, the system resets the plurality of rows of pixels of the rolling shutter imager before illuminating the tissue of the subject with the primary visible-light illumination pulse of the pulsed visible-light illumination source. For example, the system can reset the plurality of rows of pixels of the rolling shutter imager comprises triggering a synchronous frame reset functionality of the rolling shutter imager.

Example One of the Illumination Scheme

Figure 5A:
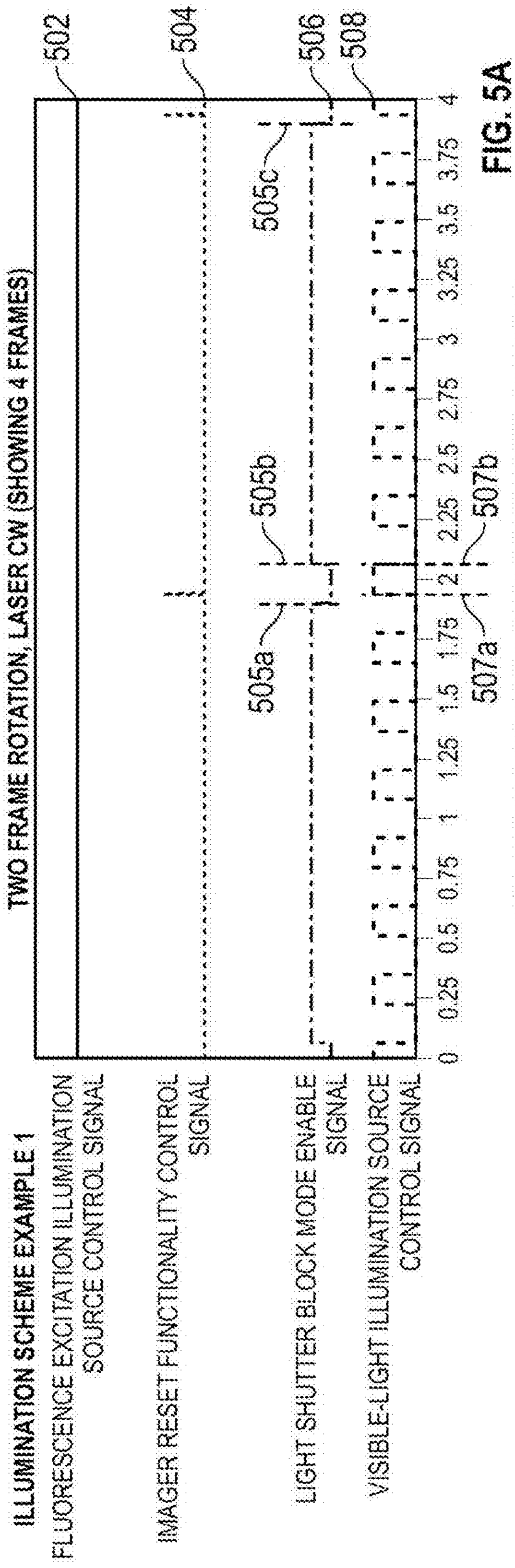
FIG. 5A illustrates exemplary operations of an exemplary imaging system, in accordance with some examples.
Figure 5B:
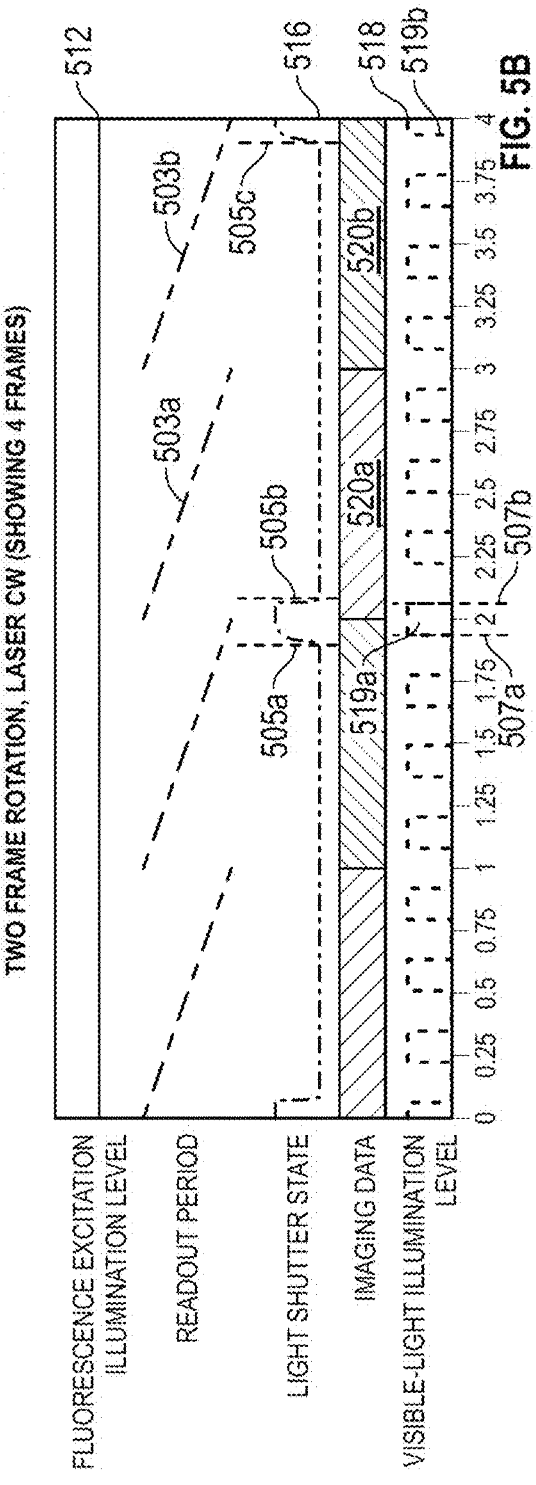
FIG. 5B illustrates a timing diagram of the exemplary imaging system, in accordance with some examples.

FIGS. 5A and 5B illustrate timing diagrams for operating an imaging system for imaging tissue from a subject, in accordance with some examples. The imaging system can include a rolling shutter imager, a fluorescence excitation illumination source, a visible-light illumination source, and a light shutter. The imaging system can illuminate the tissue of the subject using a combination of the fluorescence excitation illumination source and the visible-light illumination source to accumulate charge at a plurality of rows of pixels of the rolling shutter imager, as described herein.

The fluorescence excitation illumination source can be configured to provide fluorescence excitation illumination (e.g., infrared light) to the tissue to be imaged. The fluorescence excitation illumination can excite fluorescent markers in the tissue to emit light that in turn can reach the rolling shutter imager to generate fluorescence imaging data. In some examples, the fluorescence excitation illumination source can comprise a laser diode, such as a near-infrared (NIR) excitation light.

The visible-light illumination source can generate visible illumination light (such as any combination of red, green, and blue light) to illuminate the tissue to generate reflected light that in turn can reach the rolling shutter imager to generate visible-light imaging data. In some examples, the visible-light illumination source can comprise multiple discrete light generation components (e.g., multiple LEDs of different colors). In some examples, the visible-light illumination source can comprise a RGB light, such as an LED pulsing at a rate of 120 Hz.

In some examples, the rolling shutter imager can include a complimentary metal-oxide-semiconductor (CMOS) sensor having an array of pixels arranged in rows of pixels and columns of pixels. In some examples, the rolling shutter imager can output image frames at the CMOS sensor's frame rate (e.g., 120 Hz), which can be used to generate an image display output. The rolling shutter imager can include a mechanical shutter that can be used, for example, to control exposure of the CMOS sensor and/or to control an amount of light received at the CMOS sensor. In some examples, the rolling shutter imager can include a RGB prism camera with rolling shutter sensors. In some examples, the rolling shutter imager can include a single-sensor camera with a Bayer-filter rolling shutter sensor. The shutter of the rolling shutter imager can be an electronic shutter set to full-frame acquisition (e.g., 8.3333 ms on each line, with readout times staggered as per the rolling shutter architecture).

The light shutter has an open state and a closed state and can transition between the two states based on a control signal for operating the light shutter, as described herein. In some examples, the light shutter is a liquid crystal (LC) shutter. As discussed above, the light shutter can behave differently for a light reflected from illumination of a tissue of the subject by the visible-light illumination source and a light reflected from illumination of a tissue of the subject by the fluorescence excitation illumination source. Specifically, the light shutter can, in the open state, allow the passage of the light reflected from illumination of the tissue of the subject with the visible-light illumination such that the reflected light can reach the rolling shutter imager. In the closed state, the light shutter can prevent the light reflected from illumination of the tissue of the subject from reaching the rolling shutter imager or significantly attenuate the reflected light reaching the rolling shutter imager.

In contrast, regardless of which state the light shutter is in (e.g., the open state, the closed state, the transitioning state from the open state to the closed state, the transitioning state from the closed state to the open state), the light shutter can always allow the passage of a light emitted due to illumination of the tissue of the subject with the fluorescence excitation illumination source. In other words, the light shutter can transmit the light emitted due to illumination of the tissue of the subject with the fluorescence excitation illumination even when the light shutter is in the closed state, so the opening and/or closing of the light shutter only affects the passage of the light reflected from illumination of the tissue of the subject with the visible-light illumination. When the light shutter is in the closed state, no light reflected from illumination of the tissue of the subject with the visible-light illumination source is transmitted; instead, only the light emitted due to illumination of the tissue of the subject with the fluorescence excitation illumination source is transmitted.

In some examples, the light shutter is an electronically formed shutter. In some examples, the light shutter is a liquid crystal (LC) shutter. The light shutter is configurable to switch between the open state and the closed state in a relatively short period of time comparing to the frame rate of the imaging system. In some examples, the time for the light shutter to transition from one state to the other state can be lower than 17 milliseconds. In some examples, the time for the light shutter to transition from one state to the other state can be lower than 10 milliseconds. It should be appreciated by one of ordinary skill in the art that the time to transition from the open state to the closed state may be differ from the time to transition from the closed state to the open state due to the nature of the liquid crystal material. In some examples, the light shutter is configurable to switch from the closed state to the open state in less than 1.8 milliseconds and transition from the open state to the closed state in less than 100 microseconds. In some examples, the light shutter can be configured to operate in accordance with reversed timing (e.g., switching from the closed state to the open state in less than 100 microseconds and transition from the open state to the closed state in less than 1.8 milliseconds). It should be appreciated that the ranges described herein are merely exemplary and are not intended to be limiting.

The light shutter may be placed in any location in front of the optical sensors of the rolling shutter imager of the imaging system. In some examples, the light shutter is placed behind a unit of one or more lens (hereinafter a "lens unit") and in front of the optical sensors. In some examples, the light shutter is placed in front of the lens unit or within lens unit. In some examples, the light shutter is placed in front of an optical prism of the imaging system. In some examples, the light shutter can comprise multiple sub-shutters (e.g., corresponding to multiple optical sensors of the rolling shutter imager).

FIG. 5A illustrates control signals for operating various components of the imaging system, in accordance with some examples. Specifically, FIG. 5A illustrates a control signal 502 for operating the fluorescence excitation illumination source, a control signal 504 for operating an optional reset functionality of the rolling shutter imager, a control signal 506 for operating the light shutter, and a control signal 508 for operating the visible-light illumination source.

With reference to FIG. 5A, the control signal 502 for operating the fluorescence excitation illumination source is continuously high. Accordingly, the fluorescence excitation illumination source is continuously on to provide constant fluorescence excitation illumination to the tissue of the subject during an imaging session. Further with reference to FIG. 5A, the control signal 508 for operating the visible-light illumination source is modulated rather than being constantly on. Specifically, the control signal 508 for operating the visible-light illumination source comprises a sequence of control signal pulses. Each control signal pulse of the control signal 508 can cause the visible-light illumination source to be activated and to generate a visible-light illumination pulse for the duration of the pulse width. In one example of the illumination scheme, the frequency of the control signal 508 for operating the visible-light illumination source can be 420 Hz. In each of the timing diagrams FIGS. 5A-B, 6A-B, 7A-B, 8A-B, and 9A-B, the values on the x-axis indicate fractional or whole frame periods rather than absolute time units. Accordingly, the timing diagrams do not depict any particular frequencies.

Further with reference to FIG. 5A, the control signal 506 for operating the light shutter controls the timing for transitioning the light shutter between the closed state and the open state. In the depicted example, the control signal 506 dictates when to enable a "block mode (i.e., the closed state) of the light shutter. At any given time, the control signal 506 can be either high (indicating that the "block mode" is enabled) or low (indicating that the "block mode" is disabled).

Further with reference to FIG. 5A, the control signal 504 controls the timing for activating the reset functionality of the rolling shutter imager. In some examples, the reset functionality is the "synchronous frame reset" functionality of the rolling shutter imager. In a rolling shutter imager, all rows of pixels in the image sensor can be reset simultaneously or within a short time period (e.g., shorter than a line-by-line offset period of the rolling shutter) using the synchronous frame reset functionality. The reset functionality helps by removing artifacts (e.g. white light leaking into parts of the fluorescence frame) from the open transition of shutter. Optionally it can be skipped, and the artifacts can be removed by other means (e.g., by masking the bottom lines). In any of the examples described herein, the reset functionality may be optional.

At time 505*a*, the control signal 506 for operating the light shutter changes from high (i.e., block mode enabled) to low (i.e., block mode disabled) to cause the light shutter to transition from the closed state to the open state. Then at time 505*b*, the control signal 506 for operating the light shutter changes from low (i.e., block mode disabled) to high (i.e., block mode enabled) to cause the light shutter to transition from the open state to the closed state. As discussed in more detail in FIG. 5B, the disabling of the block mode of the light shutter (between the time 505*a* and the time 505*b*) causes the light shutter to allow the passage of light reflected from illumination of the tissue of the subject with the visible-light illumination pulse (generated by the control signal 508 between the time 507*a* and the time 507*b*). Further, regardless of the state of the light shutter, the light shutter always allows the passage of the light emitted due to illumination of the tissue of the subject with the fluorescence excitation illumination source (generated by the control signal 502) to reach the rolling shutter imager.

FIG. 5B illustrates a timing diagram for generating imaging data by operating an imaging system based on the control signals depicted in FIG. 5A, in accordance with some examples. The x-axis (i.e., time) of the timing diagram in FIG. 5A is aligned with the x-axis (i.e., time) of the timing diagram in FIG. 5B. The alignment of the axes illustrates how the control signals in FIG. 5A dictate the illumination level 512 of the fluorescence excitation illumination source over time, the illumination level 518 of the visible-light illumination source over time, the state 516 of the light shutter over time, the readout periods 503*a-b*, and the generation of imaging data 520*a* and 520*b* in FIG. 5B.

With reference to FIG. 5B, the illumination level 512 of the fluorescence excitation illumination source is constantly high, indicating that the fluorescence excitation illumination is continuously provided by the fluorescence excitation illumination source throughout the imaging session. This is because the control signal 502 for operating the fluorescence excitation illumination source in FIG. 5A is set to be continuously high.

Further with reference to FIG. 5B, the illumination level 518 of the visible-light illumination source is shown to comprise a sequence of visible-light illumination pulses. This is because the control signal 508 for operating the visible-light illumination source in FIG. 5A comprises a sequence of control signal pulses. As discussed above, each control signal pulse of the control signal 508 can cause the visible-light illumination source to be activated and to generate a visible-light illumination pulse for the duration of the pulse width. Accordingly, the control signal 508 for operating the visible-light illumination source in FIG. 5A generates a sequence of visible-light illumination pulses 518 in FIG. 5B.

Further with reference to FIG. 5B, the light shutter state 516 shows that the light shutter is generally in the closed state but is transitioned into the open state periodically in accordance with the control signal 506 for operating the light shutter in FIG. 5A. For example, at time 505*a*, the light shutter starts to transition from the closed state to the open state in accordance with the control signal 506 for operating the light shutter at the time 505*a* in FIG. 5A. Further, at time 505*b*, the light shutter starts to transition from the open state to the closed state in accordance with the control signal 506 for operating the light shutter at the time 505*b* in FIG. 5A. Between the time 505*a* (when the light shutter starts to transition from the closed state to the open state) and the time 505*b* (when the light shutter starts to transition from the open state to the closed state), the light shutter allows the passage of light reflected from illumination of the tissue of the subject with the visible-light illumination pulse 519*a* to reach the rolling shutter to generate visible-light imaging data 520*a*.

Figure 5C:
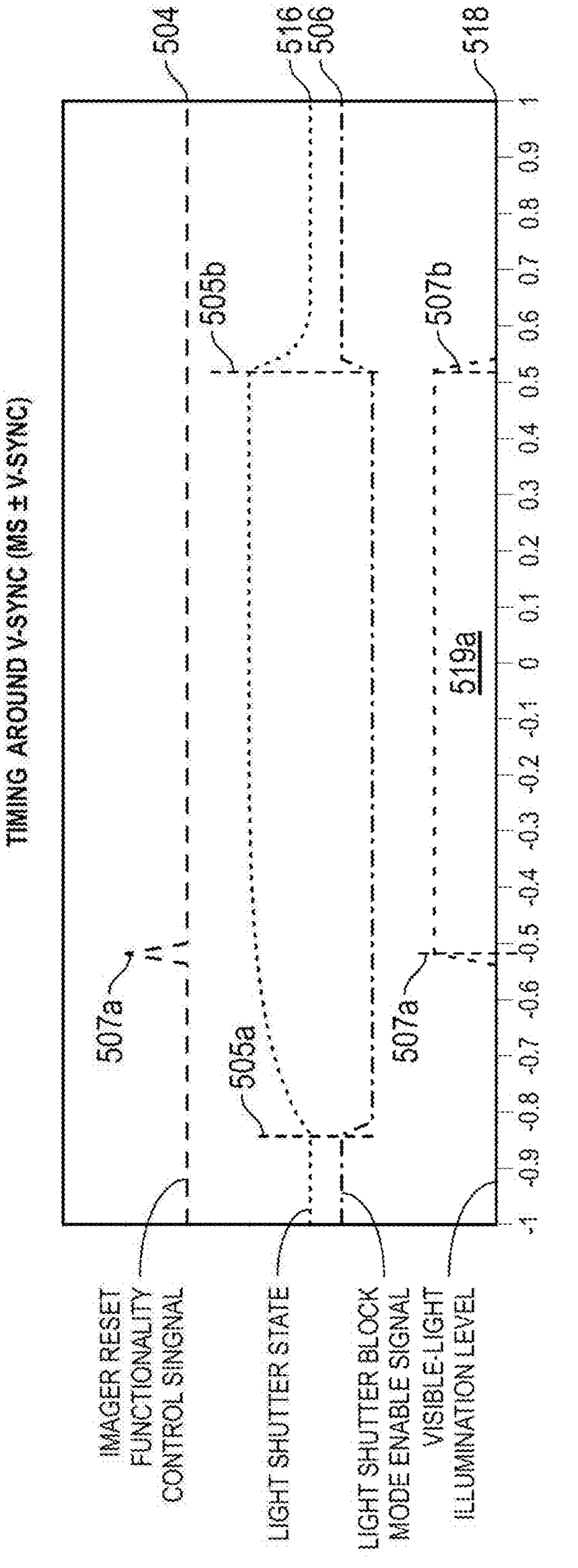
FIG. 5C illustrates a timing diagram of the exemplary imaging system, in accordance with some examples.

FIG. 5C illustrates a timing diagram with a zoomed-in view of the time period around the visible-light illumination pulse 519*a* of the visible-light illumination source, in accordance with some examples. The x-axis of the timing diagram represents time in milliseconds relative to a vertical synchronization event (V-sync). Specifically, FIG. 5C illustrates the control signal 504 for operating the reset functionality, the control signal 506 for controlling light shutter, the state 516 of the light shutter controlled by the control signal 506, and the illumination level 518 of the visible-light illumination source.

With reference to FIG. 5C, at the time 505*a*, the control signal 506 for operating the light shutter changes from high (i.e., block mode enabled) to low (i.e., block mode disabled). In response to the control signal 506, the light shutter starts to transition from the closed state to the open state starting at time 505*a*, as shown by the gradual upward curvature of the light shutter state 516 on a millisecond time scale starting from the time 505*a*. The gradual upward curvature of the light shutter state 516 indicates that the light shutter does not instantly transition from the closed state to the open state. Rather, the transitioning is gradual over time and thus the amount of light passage increases over time during the transitioning. It should be appreciated by one of ordinary skill in the art that the gradual nature of the transitioning is due to the nature of the liquid crystal material.

Then at the time 505*b*, the control signal 506 for operating the light shutter changes from low (i.e., block mode disabled) to high (i.e., block mode enabled). In response to the control signal 506, the light shutter starts to transition from the open state to the closed state starting at the time 505*b*. The rapid downward curvature of the light shutter state 516 indicates that light shutter does not instantly transition from the open state to the closed state. Rather, the transitioning is gradual over a very short time and thus the amount of light passage decreases over that time due to the nature of the liquid crystal material.

Notably in FIG. 5C, the visible-light illumination source is activated to provide a visible-light illumination pulse 519*a* at the time 507*a*, which is after the time 505*a*. As shown in FIG. 5C, the transitioning of the light shutter from the closed state to the open state is complete or substantially complete when the visible-light illumination pulse 519*a* starts at the time 507*a*, thus allowing the passage of the light reflected from illumination of the tissue of the subject with the visible-light illumination pulse 519*a* to reach the rolling shutter imager. Further, the controls signal 504 for operating the reset functionality triggers, at time 507*a*, the optional resetting of all rows of pixels in the image sensor of the rolling shutter imager simultaneously or within a short time period (e.g., shorter than a line-by-line offset period of the rolling shutter).

Further in FIG. 5C, the visible-light illumination source is deactivated to end the visible-light illumination pulse 519*a* at the time 507*b*, which in the depicted example is the same as the time 505*b* when the light shutter starts to transition to the closed state. This way, the transitioning of the light shutter to the closed state would not block the passage of the light reflected from illumination of the tissue of the subject with the visible-light illumination pulse 519*a*. Further, the transitioning of the light shutter from the open state to the closed state is complete before the next visible-light illumination pulse 519*b* (in FIG. 5B) starts. As discussed herein, the next visible-light illumination pulse 519*b* (in FIG. 5B) is a compensating pulse and is blocked by the light shutter from reaching the rolling shutter imager.

With reference to FIG. 5C, the timing of the visible-light illumination pulse 519*a* is centered around V-sync such that the center of the visible-light illumination pulse 519*a* aligns with the central "0" value of the x-axis (i.e., time). With the visible-light illumination pulse 519*a* centered around V-sync, the visible-light illumination affects all lines of the image frame whose readout period begins at that V-sync (e.g., imaging data 520*a* in FIG. 5B), in addition to the last few lines of the previous image frame.

In another embodiment, the opening of the shutter (505*a*) starts earlier to allow enough time for the open transition to complete before the start of the visible-light illumination pulse 519*a*. In this embodiment the visible light illumination pulse 519*a* is also shifted so that it starts and ends later. With this shift the period from opening of the shutter (505*a*) to the end of the light pulse (507*b*) is approximately centered to V-sync. This allows to have the same number of lines polluted on the top and the bottom of the image.

Returning to FIG. 5B, the light shutter is controlled by the control signal 506 in FIG. 5A to periodically open (e.g., at 505*a*, at 505*c*) each time to allow the reflected light from illumination of the tissue of the subject with a single visible-light illumination pulse (e.g., 519*a*, 519*b*) to pass through the light shutter and reach the rolling shutter imager. These visible-light illumination pulses (e.g., 519*a*, 519*b*) are referred to as "primary" visible-light illumination pulses. Between two neighboring primary visible-light illumination pulses, there can be one or more "compensating" visible-light illumination pulses. In the depicted example, between two neighboring primary visible-light illumination pulses (e.g., 519*a* and 519*b*), there are six compensating visible-light illumination pulses. As shown in FIG. 5B, the light shutter is in a closed state during the compensating visible-light illumination pulses, thus preventing the reflected light from illumination of the tissue of the subject with the compensating visible-light illumination pulses from passing through the light shutter to reach the rolling shutter imager.

Although the compensation pulses are not utilized by the rolling shutter imager to generate imaging data, the presence of the compensating visible-light illumination pulses can improve a user's visual comfort when the imaging system is in operation. Without the compensating visible-light illumination pulses, the primary visible-light illumination pulses alone can occur at a frequency (e.g., 60 Hz) low enough to generate a visual strobe effect, which can be uncomfortable for the user (e.g., a medical practitioner such as a surgeon) and thus compromise patient safety. By increasing the number and frequency of pulses via added compensating visible-light illumination pulses, the visible-light illumination source can appear to generate a more continuous light, which can increase the user's visual comfort. For example, with a small number of compensating visible-light illumination pulses (e.g., 1 to 3 pulses), the pulses can occur at a frequency of 120 to 240 Hz. This produces visible-light illumination that appears continuous to the human eye, but causes a strobe effect on illuminated objects as they move across the field of illumination. The strobe effect decreases as the number of compensating visible-light illumination pulses increases and can be effectively imperceptible to the user with 6 compensating visible-light illumination pulses (e.g., the pulses occur at a frequency of 420 Hz). The maximum number of compensating visible-light illumination pulses is bounded by the off period between the pulses needing to be longer than the ramp-open time of the light shutter, and the on period of each pulse needing to be long enough to acquire a reasonably bright image. In any of the examples described herein, the compensating visible-light illumination pulses preferably may have the same duration as the "primary" visible-light illumination pulses for the best user's visual comfort.

FIG. 5B further illustrates a series of readout periods (e.g., readout period 503*a*, readout period 503*b*) and the resulting imaging data (e.g., imaging data 520*a*, imaging data 520*b*). As discussed above, the light shutter starts to transition from the closed state to the open state at the time 505*a* to allow light reflected from illumination of the tissue of the subject with the primary visible-light illumination pulse 519*a* of the pulsed visible-light illumination source to reach the rolling shutter image and to cause accumulation of charge at a plurality of rows of pixels of the rolling shutter imager. The light shutter then transitions to the closed state at the time 505*b* to block the rolling shutter imager from receiving light reflected from illumination of the tissue of the subject with one or more compensating visible-light illumination pulses of the pulsed visible-light illumination source after the primary visible-light illumination pulse 519*a*.

During the readout period 503*a*, the system sequentially reads a first set of accumulated charge at the plurality of rows of pixels from a first row to a last row of the plurality of rows to produce a first set of imaging data 520*a*. The readout period 503*a* is illustrated as a diagonal line in FIG. 5B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially.

The imaging data 520*a* obtained during the readout period 503*a* contains data resulting from both the visible-light illumination and the fluorescence excitation illumination. The light shutter is open to allow passage of light reflected from illumination of the tissue of the subject with the primary visible-light illumination pulse 519*a* to reach the rolling shutter imager. The fluorescence excitation illumination source is constantly on to illuminate the tissue of the subject and the resulting reflected light always passes through the light shutter to reach the rolling shutter imager. Accordingly, the plurality of rows of pixels of the rolling shutter imager receive light from both the primary visible-light illumination pulse 519*a* and the fluorescence emission due to illumination of the tissue with the excitation illumination source. Thus, the imaging data 520*a* contains both reflected visible-light illumination data and fluorescence data.

At the end of the readout period 503*a*, the accumulated charge at the plurality of rows can be cleared. As shown in FIG. 5B, the light shutter remains in the closed state after the accumulated charge at the plurality of rows are cleared at the end of the readout period 503*a* and throughout the readout period 503*a*. After the accumulated charge at the plurality of rows are cleared at the end of the readout period 503*a*, the tissue of the subject is no longer illuminated with the visible-light illumination source due to the closed shutter but continues to be illuminated by the fluorescence excitation illumination source. During the readout period 503*b*, the system sequentially reads a second set of accumulated charge from the first row to the last row of the plurality of rows of pixels to produce a second set of imaging data 520*b*. The readout period 503*b* is also illustrated as a diagonal line in FIG. 5B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially for the rolling shutter architecture.

The imaging data 520*b* obtained during the readout period 503*b* contains data resulting from the fluorescence emission and not from the visible-light illumination. Because the light shutter is closed at the end of the readout period 503*a* and throughout the readout period 503*a* and most of the readout period 503*b*, light reflected from illumination of the tissue of the subject by the visible-light illumination source (in this case, the compensating visible-light illumination pulses following the primary visible-light illumination pulse 519*a*) are blocked from reaching the rolling shutter imager. However, because the fluorescence excitation illumination source is constantly on, fluorescence light emitted due to illumination of the tissue of the subject by the fluorescence excitation illumination source passes through the closed light shutter and reaches the rolling shutter imager. Accordingly, the imaging data 520*b* contains only fluorescence data for the majority of the rows.

Further with reference to FIG. 5B, the imaging system can generate one or more image frames based on the first set of imaging data (e.g., imaging data 520*a*) obtained during the first readout period 503*a* and/or the second set of imaging data (e.g., imaging data 520*b*) obtained during the second readout period 503*b*. The scheme in FIGS. 5A and 5B involves a series of two-image rotations. In each two-image rotation, two sets of imaging data (e.g., imaging data 520*a* and 520*b*) are acquired and the next two-image rotation starts. In FIG. 5B, the first readout period 503*a* and the second readout period 503*b*, taken together, form a two-frame image acquisition rotation. Multiple image acquisition rotations can be performed when imaging the tissue of the subject (i.e., these steps can be repeated).

In the depicted example, the imaging system can generate a visible-light image frame based on the first set of imaging data and a fluorescence image frame based on the second set of imaging data. Another type of image frame can be a blended image frame based on both the fluorescence image frame and the visible-light image frame. In some examples, the fluorescence image frame can be overlaid on the visible-light image frame in the blended image frame. In some examples, the blended image frame can be derived from colorizing the visible-light image frame based on the fluorescence image frame (e.g., based on the ratio of the fluorescence image frame to one or more channels of the visible-light frame). The generated image frames can be added to a video stream and displayed on a display to a user (e.g., a medical practitioner such as a surgeon).

In some examples, the imaging system can produce about 60 fluorescence image frames and 60 visible-light image frames per second, with each frame exposed to either only the fluorescence excitation illumination source or both illumination sources at the same time. In other words, the imager can output image frames at the sensor frame rate of 120 Hz, which are then processed (e.g., in a control unit of the imaging system) to generate the display output (e.g., the video stream). In one example of the illumination scheme, a blended image can be generated every 1/60 s (i.e., at 60 Hz). Thus, if the rolling shutter imager were configured to output the blended images, the display output frame rate would be 60 fps. Each blended frame can be based on a combination of one or more visible-light image frames and one or more fluorescence image frames.

Figure 5D:
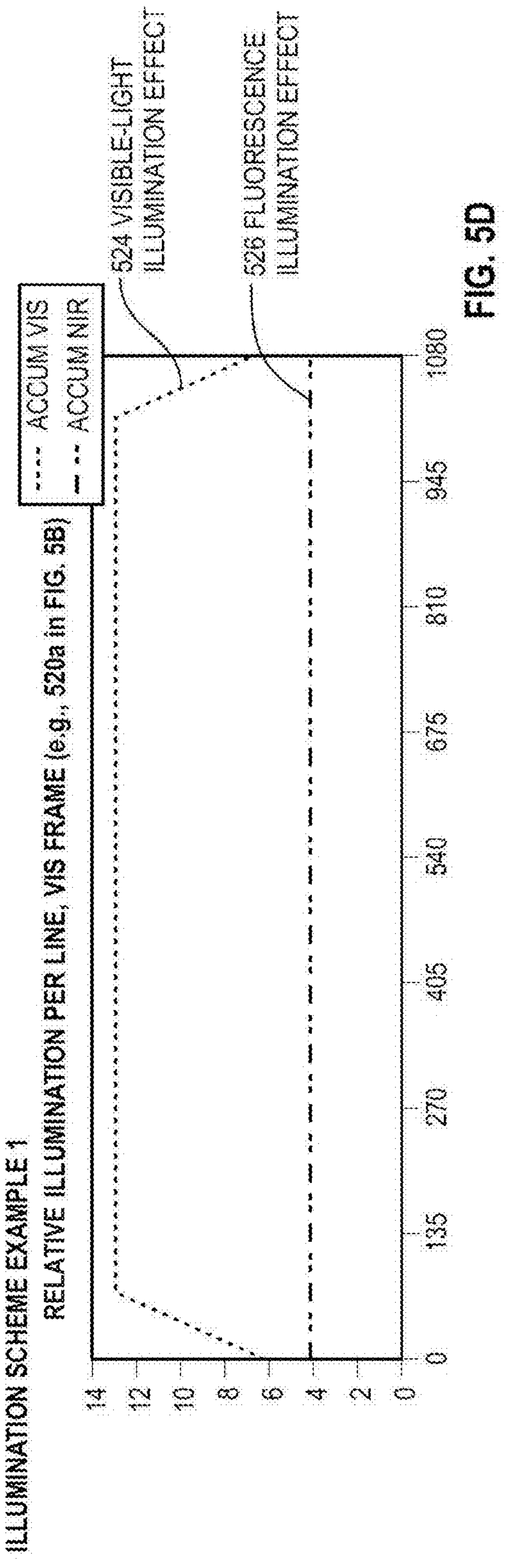
FIG. 5D illustrates the relative effect of each illumination source on a visible-light image frame, in accordance with some examples.
Figure 5E:
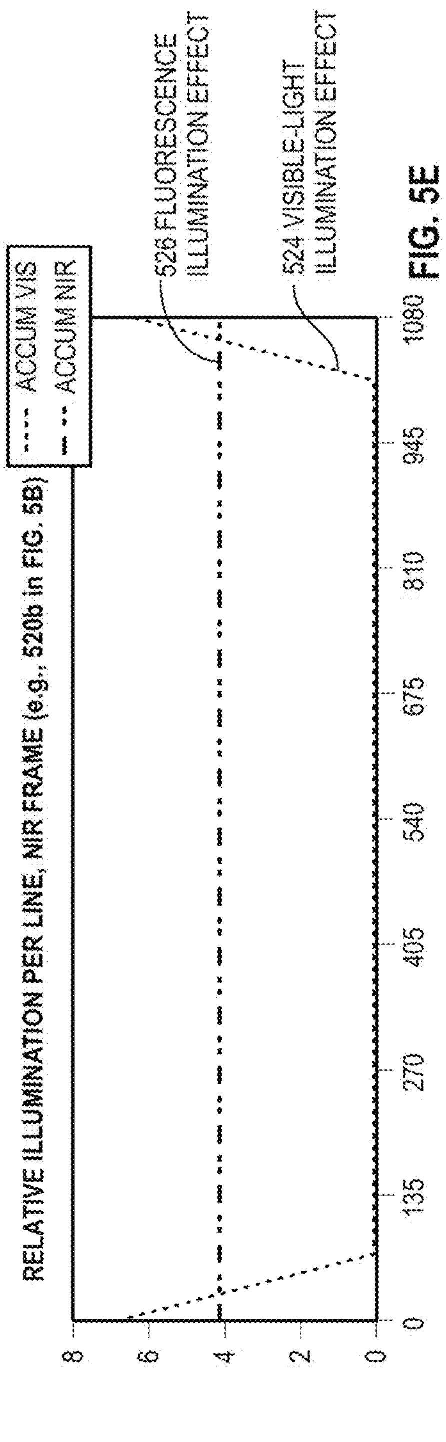
FIG. 5E illustrates the relative effect of each illumination source on a fluorescence image frame, in accordance with some examples.

FIGS. 5D and 5E illustrate the effects of the visible-light illumination source and the fluorescence excitation illumination source on each line of an image frame, in accordance with some examples. For each image frame, lines range from line 0 to line 1080, as shown by the x-axis of each figure. In some examples, line 0 can correspond to the top line of pixels of the image frame. Line 1080 can correspond to the bottom line of pixels of the image frame. Although the depicted example assumes that the rolling shutter imager is a 1080-line HD image sensor, the imaging can also be performed on higher or lower resolution image sensors. In FIGS. 5D and 5E, the y-axis represents the amount of effect of each illumination source. The effect 524 indicates, for each line of the image frame, the amount of effect from light reflected from illumination of a tissue of the subject by the visible-light illumination source. The effect 526 indicates, for each line of the image frame, the amount of effect from fluorescence light due to illumination of a tissue of the subject by the fluorescence excitation illumination source.

FIG. 5D illustrates the relative effect (in arbitrary units) of each illumination source on a visible-light image frame, which may correspond to imaging data 520*a* in FIG. 5B. In the visible-light image frame, light reflected from illumination of a tissue of the subject by the visible-light illumination source reaches the rolling shutter imager, affecting each line of the visible-light image frame as shown by effect 524. In the depicted example, the effect 524 rises from about half scale to full scale in the first few lines of the frame, then remains constant for most lines, then decreases to about half scale in the last few lines of the frame. The effect 526 of the fluorescence excitation illumination source remains constant on all lines due to the constant illumination provided by the fluorescence excitation illumination source. As shown, the effect 526 of the fluorescence excitation illumination source on the visible-light image frame is relatively small compared to the effect 524 of the visible-light illumination source. Thus, the effect 526 can be removed to extract only the effect 524 of the visible-light illumination source. This can be performed by subtracting the corresponding fluorescence image frame (e.g., imaging data 520*b* in FIG. 5B) of each image acquisition rotation from the visible-light image frame, or can simply be ignored.

FIG. 5E illustrates the relative effect of each illumination source on a fluorescence image frame, which may correspond to imaging data 520*b* in FIG. 5B. Unlike the visible-light image frame of FIG. 5D, in the fluorescence image frame, reflected visible-light illumination is blocked by the light shutter for most of the lines. The effect 524 indicates low values for the first few and last few lines of the image frame and 0 for the remaining lines. In comparison, in the fluorescence image frame, the effect 526 of the fluorescence excitation illumination source remains constant due to the constant illumination provided by the fluorescence excitation illumination source.

In FIGS. 5D and 5E, the effect 524 of the visible-light illumination source can pollute the first approximately 71 lines and last approximately 68 lines of each image frame. The exact number of polluted lines can depend on the on-period for the visible-light illumination source. The polluted lines are denoted by the diagonal portions of the effect 524 near line 0 and line 1080 (e.g., the first 71 lines and the last 68 lines) and can produce visual artifacts upon the generation of the image frame. Accordingly, the polluted lines can be trimmed off in processing (e.g., the top and bottom of each image frame can be masked to remove the resulting artifacts).

In some modes of operation, the user might be interested in the maximum signal quality for the fluorescence frame while not requiring a white-light frame. In this "contrast" mode the imaging system produces a black and white (or colorized) image of the fluorescence. For this mode, the light shutter remains closed throughout the imaging sequence and functions as a visible-light filter. The image acquisition only acquires the fluorescence frame utilizing a long exposure time which is close to the frame period.

Alternative Example One of the Illumination Scheme

In the imaging system described in FIGS. 5A-5E above, the fluorescence excitation illumination source is constantly on, thus providing maximum exposure time for the fluorescence image frames and providing maximum fluorescence excitation strength over the entire range of working distances (e.g., the distance from the front lens element of the camera to the tissue being observed). However, when the tissue to be imaged is close to the imaging system that is emitting the illumination (e.g., at the minimum working distance), the fluorescence excitation strength can be excessively high and cause an intense fluorescence emission that, in turn, can generate a strong fluorescence signal in the rolling shutter imager of the imaging system. Because each image frame generated by the imaging system can have a fluorescence component, the strong fluorescence signal generated by the emission can reduce the background white-light average luminance and contaminate the image frame. Accordingly, in some examples, it can be desirable to reduce the fluorescence excitation strength provided by the fluorescence excitation illumination source.

Figure 6A:
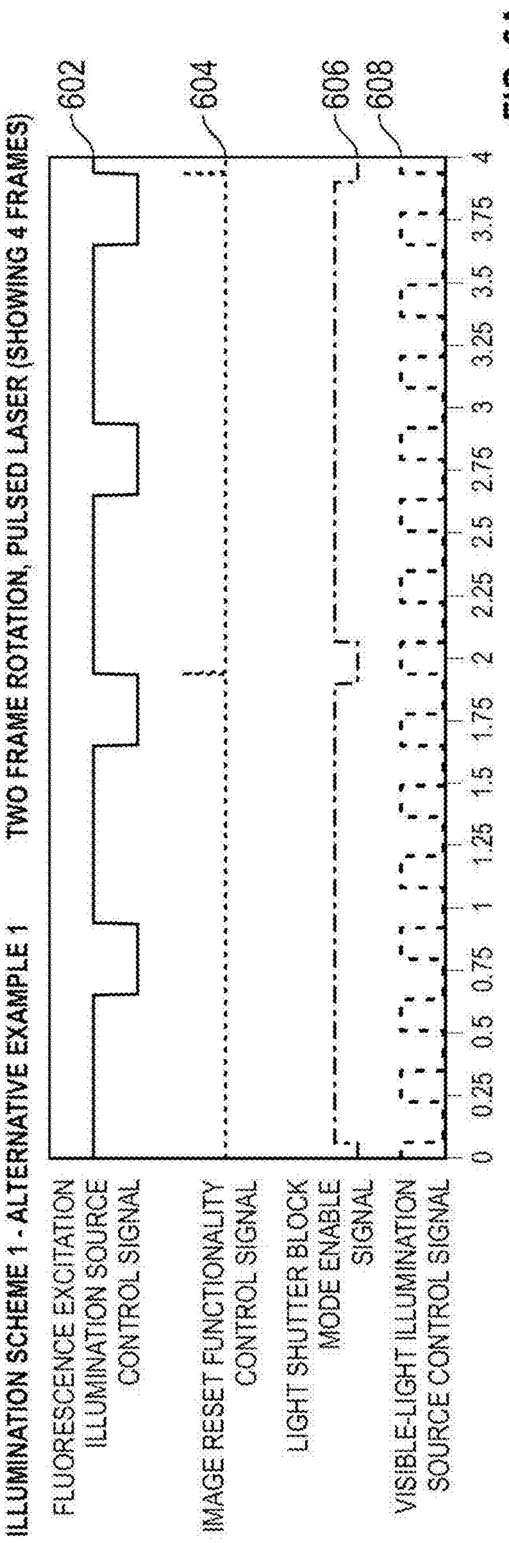
FIG. 6A illustrates exemplary operations of an exemplary imaging system, in accordance with some examples.
Figure 6B:
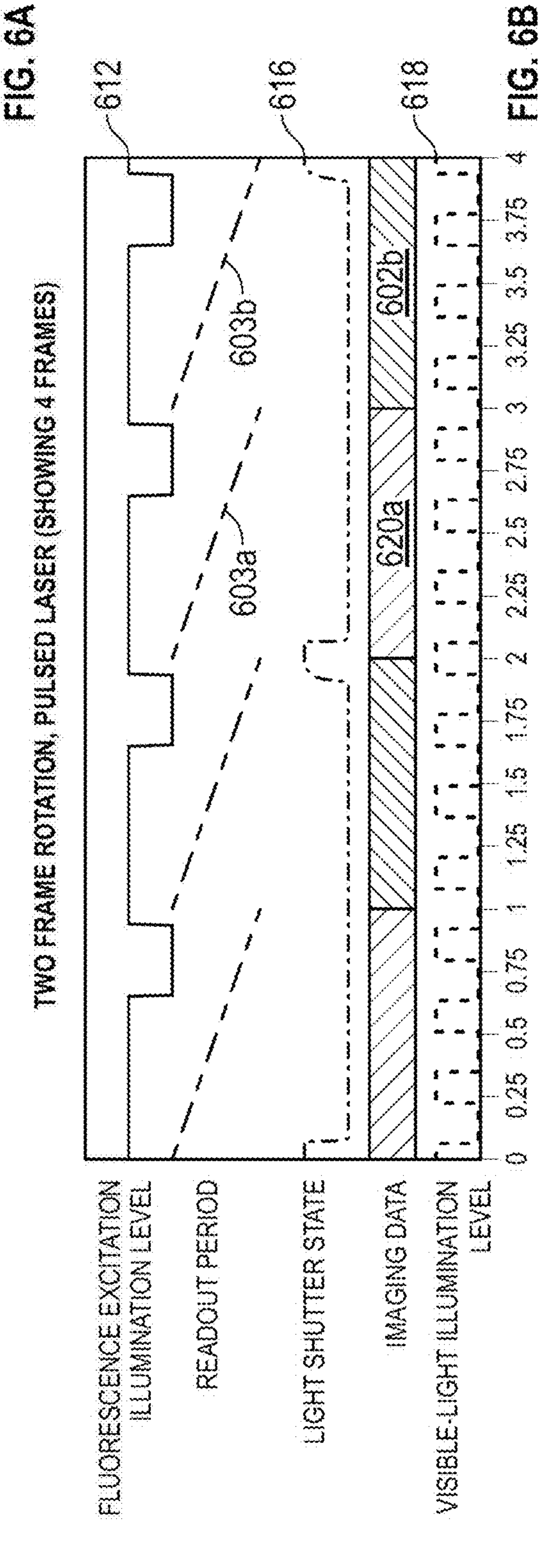
FIG. 6B illustrates a timing diagram of the exemplary imaging system, in accordance with some examples.

FIGS. 6A and 6B illustrate timing diagrams for operating an imaging system for imaging tissue from a subject, in accordance with some examples. Similar to the imaging system of FIGS. 5A and 5B, the imaging system includes a rolling shutter imager, a fluorescence excitation illumination source, and a visible-light illumination source, and a light shutter. However, unlike the imaging system of FIGS. 5A and 5B, in the depicted examples for FIGS. 6A and 6B, the fluorescence excitation illumination source is set to be modulated (i.e., pulsed). This pulsing can reduce the intensity of the fluorescence excitation illumination in the set of imaging data corresponding to the fluorescence light frames (e.g., imaging data 620*b*). The pulsing can be applied evenly such that each line of the fluorescence light frames receives the same duration of fluorescence emission due to illumination of the tissue by the fluorescence excitation illumination source.

FIG. 6A illustrates control signals for operating various components of the imaging system, in accordance with some examples. Specifically, FIG. 6A illustrates a control signal 602 for operating the fluorescence excitation illumination source, a control signal 604 for operating a reset functionality of the rolling shutter imager, a control signal 606 for operating the light shutter, and a control signal 608 for operating the visible-light illumination source. The control signal 604 operates in the same manner as the control signal 504 for operating reset functionality of the rolling shutter imager of FIG. 5A. The control signal 606 operates in the same manner as the control signal 506 for operating the light shutter of FIG. 5A. The control signal 608 operates in the same manner as the control signal 508 for operating the visible-light illumination source. However, the control signal 602 for operating the fluorescence excitation illumination source differs from the always-on control signal 502 in FIG. 5A.

With reference to FIG. 6A, the control signal 602 for operating the fluorescence excitation illumination source is modulated rather than being constantly on. Specifically, the control signal 602 comprises a sequence of control signal pulses. Each control signal pulse of the control signal 602 can cause the fluorescence excitation illumination source to be activated and to provide a fluorescence excitation illumination pulse for the duration of the pulse width. In some examples, two pulses of the control signal 602 can occur during a single image acquisition rotation. In one example of the illumination scheme, the frequency of the control signal 602 for operating the visible-light illumination source can be 120 Hz.

FIG. 6B illustrates a timing diagram for generating imaging data by operating an imaging system based on the control signals depicted in FIG. 6A, in accordance with some examples. The x-axis (i.e., time) of the timing diagram in FIG. 6A is aligned with the x-axis (i.e., time) of the timing diagram in FIG. 6B. The alignment of the axes illustrates how the control signals in FIG. 6A dictate the illumination level 612 of the fluorescence excitation illumination source over time, the illumination level 618 of the visible-light illumination source over time, the state 616 of the light shutter over time, the readout periods 603*a-b*, and the generation of imaging data 620*a* and 620*b* in FIG. 6B. The illumination level 618 follows an identical timing as the illumination level 518 of the visible-light illumination source over time, as shown in FIG. 5B. The state 616 follows an identical timing as the state 516 of the light shutter over time, as shown in FIG. 5B. The readout periods 603*a-b* follow an identical timing as the readout periods 503*a-b* of FIG. 5B. The generation of imaging data 620*a* and 620*b* follows an identical timing as that of imaging data 520*a* and 520*b* of FIG. 5B.

With reference to FIG. 6B, the illumination level 612 of the fluorescence excitation illumination source is shown to comprise a sequence of fluorescence excitation illumination pulses. This is because the control signal 602 for operating the fluorescence excitation illumination source in FIG. 6A comprises a sequence of control signal pulses. As discussed above, each control signal pulse of the control signal 602 can cause the fluorescence excitation illumination source to be activated and to provide a fluorescence excitation illumination pulse for the duration of the pulse width. Accordingly, the control signal 602 for operating the visible-light illumination source generates a sequence of fluorescence excitation illumination pulses, as illustrated by the illumination level 612.

With reference to FIG. 6B, the fluorescence excitation illumination source can be pulsed such that every line of a fluorescence light frame receives the same duration of fluorescence. The readout period corresponding to the fluorescence light frames (e.g., readout period 603*b*) can remain the same duration as the readout periods of FIG. 5B. Accordingly, modulating the fluorescence excitation illumination source can reduce the fluorescence excitation strength without necessitating any changes to the readout periods and/or other timings of the imaging system relative to the imaging system of FIG. 5B. Referring back to FIG. 6B, modulating the fluorescence excitation illumination source can increase the dynamic range of the imaging system and prevent overexposing the imager to fluorescence signals. The imaging data associated with the readout period 603*b* can represent light from only the fluorescence excitation illumination source for most lines in the imaging data. Accordingly, in the depicted example, the imaging data 620*b* can comprise fluorescence light imaging data and not visible-light imaging data for most lines in the imaging data.

With reference to FIG. 6B, the pulsed fluorescence excitation illumination source is pulsed at a 71% duty cycle, as illustrated by the illumination level 612. In some examples, the duty cycle can be any duty cycle from <1% to 100%, and the duty cycle can be adjusted in order to vary the intensity of illumination provided by the fluorescence excitation illumination source. Although this has the same effect as running a constantly active (i.e., continuous-wave) fluorescence excitation illumination source at a lower current, an advantage of the pulsed fluorescence excitation illumination source is the removal of any wavelength dependence that certain laser diodes can have with respect to instantaneous current. Similarly, the effective illumination of the visible-light illumination source (as described in FIGS. 5A-5E) can be adjusted by changing the duration of the pulses (both the primary pulse and the compensation pulses), or by varying their currents. Likewise, an advantage of varying pulse duration rather than current is the wavelength stability of the individual sources.

Figure 6C:
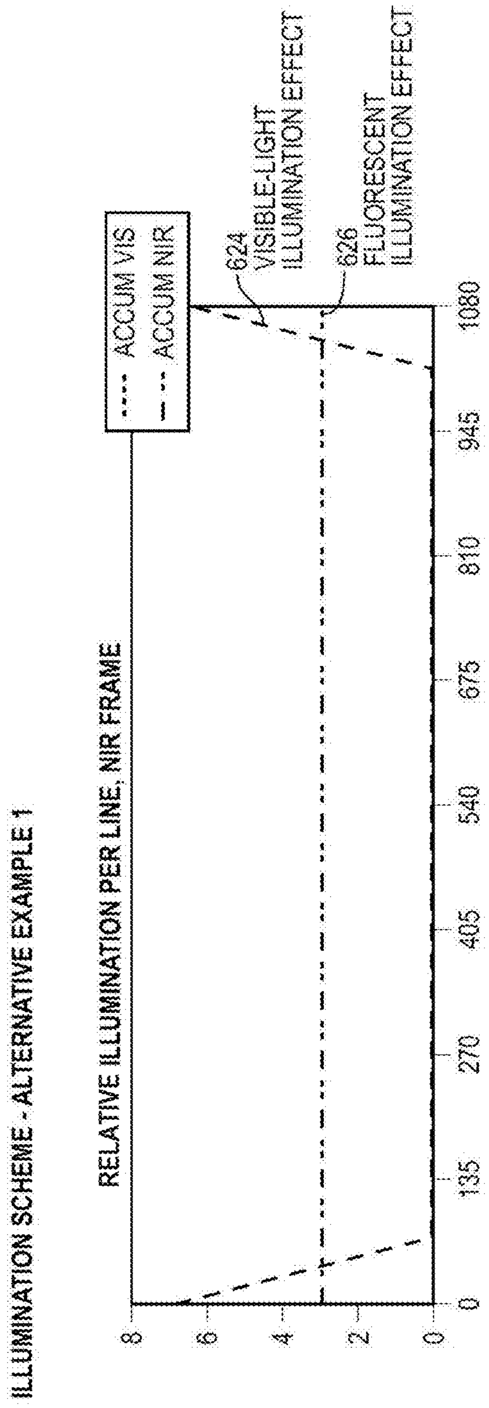
FIG. 6C illustrates the relative effect of each illumination source on a fluorescence image frame, in accordance with some examples.

FIG. 6C illustrates the relative effect of each illumination source on the fluorescence image frames, which, in the depicted example, can be obtained from imaging data 620*b*. In the fluorescence image frame, due to the light shutter, the effect 624 of the visible-light illumination source is low to none. This is represented by the effect 624 ranging between a value of 0-6 (generally 0 for most of the lines 0-1080), indicating that the visible-light illumination source does not have an effect on most lines of the visible-light image frames. However, for the fluorescence image frame, the effect 626 of the fluorescence excitation illumination source remains constant at a relative value of 3 due fluorescence emission caused by the pulsed illumination provided by the source. This is a lower value than the value of effect 526 (which represents the accumulated charge levels of the continuous-wave fluorescence excitation illumination source in FIG. 5E), which has a constant relative value of 4. Accordingly, compared to imaging systems with continuous-wave fluorescence excitation illumination, the imaging systems that utilize pulsed fluorescence excitation illumination can produce image frames associated with reduced fluorescence excitation strength.

Further with reference to FIG. 6C, the modulation of the pulsed fluorescence excitation illumination source does not affect the constancy of the accumulated charge value across the lines of the image frames, only the value itself (i.e., effect 626 has a constant value of 3). This is because the integral over one full readout period always contains exactly one pulse, no matter when it starts (e.g., one complete pulse, or the last part of one pulse and the first part of the next pulse), thus always adding up to the same total illumination provided. The modulation of the pulsed fluorescence excitation illumination source is not affected by the light shutter.

Example Two of the Illumination Scheme

Figure 7A:
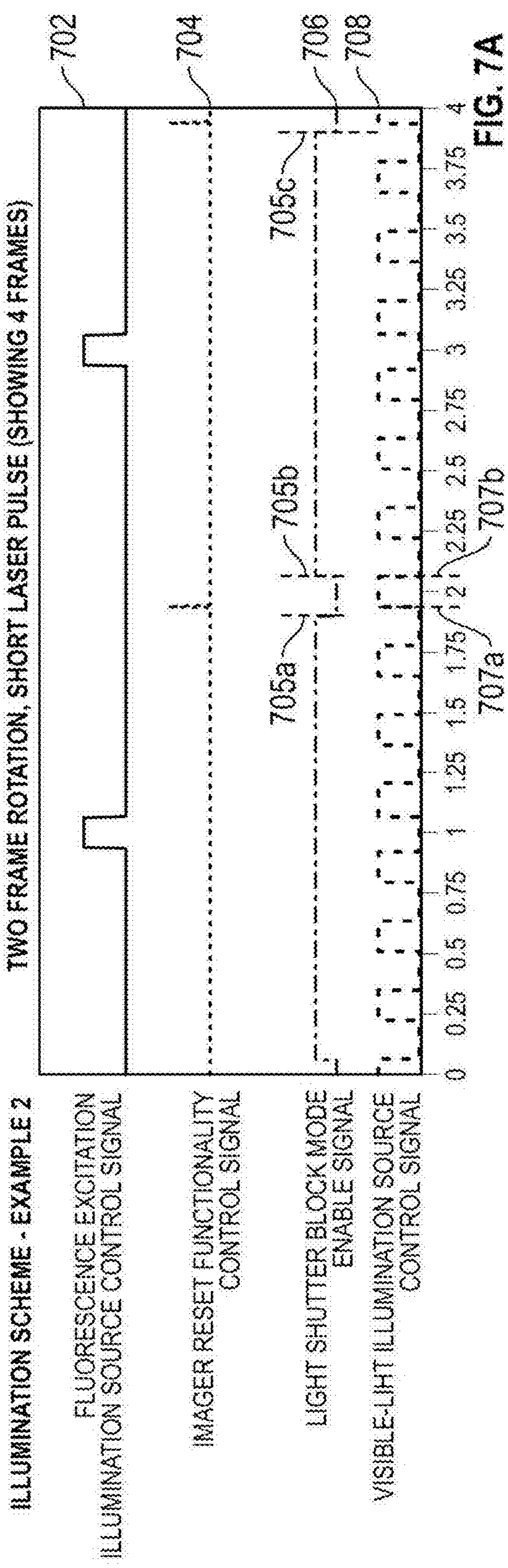
FIG. 7A illustrates exemplary operations of an exemplary imaging system, in accordance with some examples.
Figure 7B:
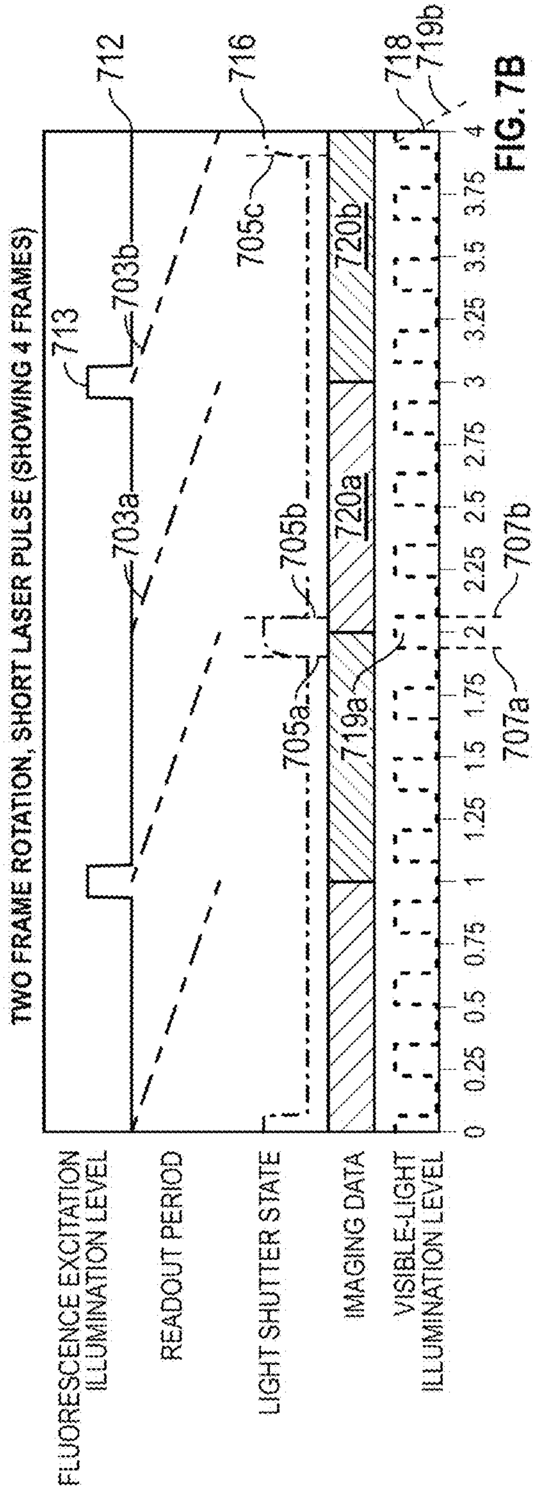
FIG. 7B illustrates a timing diagram of the exemplary imaging system, in accordance with some examples.

FIGS. 7A and 7B illustrate timing diagrams for operating an imaging system for imaging tissue of a subject, in accordance with some examples. Similar to the imaging system of FIGS. 6A and 6B, the imaging system includes a rolling shutter imager, a fluorescence excitation illumination source, and a visible-light illumination source, and a light shutter. The fluorescence excitation illumination source of the imaging system is set to be modulated (i.e., pulsed). However, unlike the imaging system of FIGS. 6A and 6B, in the depicted examples for FIGS. 7A and 7B, the fluorescence excitation illumination pulses have shorter pulse widths and are pulsed on alternate frames at the same frequency as the primary visible-light illumination pulses (i.e., only for fluorescence image frames and not for visible-light image frames).

In one example of the illumination scheme, the fluorescence excitation illumination can be pulsed at 60 Hz rather than 120 Hz (e.g., one example of FIGS. 6A and 6B). FIGS. 7A-B can be a more energy-efficient configuration for operating the fluorescence excitation illumination source because pulsing the fluorescence excitation illumination source only for fluorescence image frames means that all of the fluorescence excitation illumination is used for imaging. In contrast, when the fluorescence excitation illumination source is pulsed on every frame (e.g., FIGS. 6A-B) or constantly active (e.g., FIGS. 5A-B), at least half of the fluorescence excitation illumination is not used for imaging. By pulsing the fluorescence excitation illumination source only for fluorescence image frames, the same image quality can be achieved with half of the optical energy, half of the tissue heating, and half of the photo-bleaching effect. Furthermore, not providing fluorescence excitation illumination during visible-light illumination frames eliminates the need to correct for fluorescence in those frames.

FIG. 7A illustrates control signals for operating various components of the imaging system, in accordance with some examples. Specifically, FIG. 7A illustrates a control signal 702 for operating the fluorescence excitation illumination source, a control signal 704 for operating a reset functionality of the rolling shutter imager, a control signal 706 for operating the light shutter, and a control signal 708 for operating the visible-light illumination source.

With reference to FIG. 7A, the control signal 702 for operating the fluorescence excitation illumination source is modulated rather than being constantly on. Specifically, the control signal 702 comprises a sequence of control signal pulses. Each control signal pulse of the control signal 702 can cause the fluorescence excitation illumination source to be activated and to provide a fluorescence excitation illumination pulse for the duration of the pulse width. In some examples, one pulse of the control signal 702 can occur per image acquisition rotation, such that the fluorescence excitation illumination source is activated for the collection of imaging data for a fluorescence image frame. In one example of the illumination scheme, the frequency of the control signal 702 for operating the fluorescence excitation illumination source can be 60 Hz. The frequency and pulse width are constrained by the need to run the fluorescence excitation illumination source at a high enough instantaneous power for a short pulse duration to be sufficient for the desired fluorescence response, while remaining within optical safety limits for instantaneous power. A longer pulse width can be employed at the expense of trimming more lines from the top and bottom of the processed image.

Further with reference to FIG. 7A, the control signal 708 for operating the visible-light illumination source is modulated. Specifically, the control signal 708 comprises a sequence of control signal pulses. Each control signal pulse of the control signal 708 can cause the visible-light illumination source to be activated and to generate a visible-light illumination pulse for the duration of the pulse width. In one example of the illumination scheme, the frequency of the control signal 708 for operating the visible-light illumination source can be 420 Hz.

Further with reference to FIG. 7A, the control signal 706 for operating the light shutter controls the timing for transitioning the light shutter between the closed state and the open state. In the depicted example, the control signal 706 dictates when to enable a “block mode” (i.e., the closed state) of the light shutter. At any given time, the control signal 706 can be either high (indicating that the “block mode” is enabled) or low (indicating that the “block mode” is disabled).

At time 705*a*, the control signal 706 for operating the light shutter changes from high (i.e., block mode enabled) to low (i.e., block mode disabled) to cause the light shutter to transition from the closed state to the open state. Then at time 705*b*, the control signal 706 for operating the light shutter changes from low (i.e., block mode disabled) to high (i.e., block mode enabled) to cause the light shutter to transition from the open state to the closed state. As discussed in more detail in FIG. 7B, the disabling of the block mode of the light shutter (between the time 705*a* and the time 705*b*) causes the light shutter to allow the passage of light reflected from illumination of the tissue of the subject with the visible-light illumination pulse (generated by the control signal 708 between the time 707*a* and the time 707*b*). Further, regardless of the state of the light shutter, the light shutter always allows the passage of the light emitted due to illumination of the tissue of the subject with the fluorescence excitation illumination source (generated by the control signal 702). In fact, in the depicted example, the time periods in which the fluorescence excitation illumination source is on occur only when the light shutter is in the closed state, yet light emitted due to illumination of the tissue of the subject with the fluorescence excitation illumination source (generated by the control signal 702) is not blocked by the light shutter.

FIG. 7B illustrates a timing diagram for generating imaging data by operating an imaging system based on the control signals depicted in FIG. 7A, in accordance with some examples. The x-axis (i.e., time) of the timing diagram in FIG. 7A is aligned with the x-axis (i.e., time) of the timing diagram in FIG. 7B. The alignment of the axes illustrates how the control signals in FIG. 7A dictate the illumination level 712 of the fluorescence excitation illumination source over time, the illumination level 718 of the visible-light illumination source over time, the state 716 of the light shutter over time, the readout periods 703*a-b*, and the generation of imaging data 720*a* and 720*b* in FIG. 7B.

With reference to FIG. 7B, the illumination level 712 of the fluorescence excitation illumination source is shown to comprise a sequence of fluorescence excitation illumination pulses. This is because the control signal 702 for operating the fluorescence excitation illumination source in FIG. 7A comprises a sequence of control signal pulses. As discussed above, each control signal pulse of the control signal 702 can cause the fluorescence excitation illumination source to be activated and to provide a fluorescence excitation illumination pulse for the duration of the pulse width. Accordingly, the control signal 702 for operating the visible-light illumination source generates a sequence of fluorescence excitation illumination pulses (e.g., fluorescence excitation illumination pulse 713), as illustrated by the illumination level 712. In some examples, at least part of the fluorescence excitation illumination pulse 713 can occur during the collection of imaging data for a fluorescence image frame.

Further with reference to FIG. 7B, the illumination level 718 of the visible-light illumination source is shown to comprise a sequence of visible-light illumination pulses. This is because the control signal 708 for operating the visible-light illumination source in FIG. 7A comprises a sequence of control signal pulses. As discussed above, each control signal pulse of the control signal 708 can cause the visible-light illumination source to be activated and to generate a visible-light illumination pulse for the duration of the pulse width. Accordingly, the control signal 708 for operating the visible-light illumination source in FIG. 7A generates a sequence of visible-light illumination pulses 718 in FIG. 7B.

Further with reference to FIG. 7B, the light shutter state 716 shows that the light shutter is generally in the closed state but is transitioned into the open state periodically in accordance with the control signal 706 for operating the light shutter in FIG. 7A. For example, at time 705*a*, the light shutter starts to transition from the closed state to the open state in accordance with the control signal 706 for operating the light shutter at the time 705*a* in FIG. 7A. Further, at time 705*b*, the light shutter starts to transition from the open state to the closed state in accordance with the control signal 706 for operating the light shutter at the time 705*b* in FIG. 7A. Between the time 705*a* (when the light shutter starts to transition from the closed state to the open state) and the time 705*b* (when the light shutter starts to transition from the open state to the closed state), the light shutter allows the passage of light reflected from illumination of the tissue of the subject with the visible-light illumination pulse 719*a*.

The light shutter is controlled by the control signal 706 in FIG. 7A to periodically open (e.g., at 705*a*, at 705*c*), each time to allow the reflected light from illumination of the tissue of the subject with a single visible-light illumination pulse (e.g., 719*a*, 719*b*) to pass through the light shutter and reach the rolling shutter imager. These visible-light illumination pulses (e.g., 719*a*, 719*b*) are referred to as "primary" visible-light illumination pulses. Between two neighboring primary visible-light illumination pulses, there can be one or more "compensating" visible-light illumination pulses. In the depicted example, between two neighboring primary visible-light illumination pulses (e.g., 719*a* and 719*b*), there are six compensating visible-light illumination pulses. As shown in FIG. 7B, the light shutter is in a closed state during the compensating visible-light illumination pulses, thus preventing the reflected light from illumination of the tissue of the subject with the compensating visible-light illumination pulses from passing through the light shutter to reach the rolling shutter imager. However, the light shutter being in the closed state does not prevent fluorescence light emitted due to illumination 712 of the tissue of the subject with the fluorescence excitation illumination source (generated by the control signal 702) from passing through the light shutter to reach the rolling shutter imager.

FIG. 7B further illustrates a series of readout periods (e.g., readout period 703*a*, readout period 703*b*) and the resulting imaging data (e.g., imaging data 720*a*, imaging data 720*b*). As discussed above, the light shutter starts to transition from the closed state to the open state at the time 705*a* to allow light reflected from illumination of the tissue of the subject with the primary visible-light illumination pulse 719*a* of the pulsed visible-light illumination source to reach the rolling shutter image and to cause accumulation of charge at a plurality of rows of pixels of the rolling shutter imager. The light shutter then transitions to the closed state at the time 705*b* to block the rolling shutter imager from receiving light reflected from illumination of the tissue of the subject with one or more compensating visible-light illumination pulses of the pulsed visible-light illumination source after the primary visible-light illumination pulse 719*a*.

During the readout period 703*a*, the system sequentially reads a first set of accumulated charge at the plurality of rows of pixels from a first row to a last row of the plurality of rows to produce a first set of imaging data 720*a*. The readout period 703*a* is illustrated as a diagonal line in FIG. 7B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially.

The imaging data 720*a* obtained during the readout period 703*a* contains data resulting from the visible-light illumination. The light shutter is open to allow passage of light reflected from illumination of the tissue of the subject with the primary visible-light illumination pulse 719*a* to reach the rolling shutter imager. The fluorescence excitation illumination source is not on (as illustrated by illumination level 712 of the fluorescence excitation illumination source). Accordingly, the plurality of rows of pixels of the rolling shutter imager receive reflected illumination from only the primary visible-light illumination pulse 719*a* for most lines. Thus, the imaging data 720*a* contains only reflected visible-light illumination data and little to no fluorescence data for most lines. In some examples, fluorescence can pollute the imaging data associated with the first few rows and/or the last few rows of pixels of the imager. The polluted portions of the imaging data 720*a* can be trimmed off in processing (e.g., the top and bottom of each image frame can be masked to remove the resulting artifacts).

At the end of the readout period 703*a*, the accumulated charge at the plurality of rows can be cleared. As shown in FIG. 7B, the light shutter remains in the closed state after the accumulated charge at the plurality of rows are cleared at the end of the readout period 703*a*. After the accumulated charge at the plurality is cleared at the end of the readout period 703*a*, the tissue of the subject is not illuminated with the visible-light illumination source due to the closed shutter but begins to be illuminated by the fluorescence excitation illumination source. The timing of the 713 is centered around the beginning of the readout period 703*b* such that the center of the fluorescence excitation illumination pulse 713 aligns with the start of the readout period 703*b*. Because the fluorescence excitation illumination pulse 713 starts before the start of the readout period 703*b*, the fluorescence excitation illumination affects all lines of the image frame associated with the readout period 703*b* (e.g., imaging data 720*b*), in addition to the last few lines of the previous image frame.

During the readout period 703*b*, the system sequentially reads a second set of accumulated charge from the first row to the last row of the plurality of rows of pixels to produce a second set of imaging data 720*b*. The readout period 703*b* is also illustrated as a diagonal line in FIG. 7B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially.

The imaging data 720*b* obtained during the readout period 703*b* contains data resulting from the fluorescence emission and not from the visible-light illumination for most lines. Because the light shutter is closed before the end of the readout period 703*a* and throughout the readout period 703*b*, light reflected from illumination of the tissue of the subject by the visible-light illumination source (in this case, the compensating visible-light illumination pulses following the primary visible-light illumination pulse 719*a*) are blocked from reaching the rolling shutter imager. However, because the fluorescence excitation illumination pulse 713 occurs before the start of the readout period 703*b*, light emitted due to illumination of the tissue of the subject by the fluorescence excitation illumination source passes through the closed light shutter and reaches the rolling shutter imager before the start of the readout period 703. Accordingly, the imaging data 720*b* contains only fluorescence data for most lines.

Further with reference to FIG. 7B, the imaging system can generate one or more image frames based on the first set of imaging data (e.g., imaging data 720*a*) obtained during the first readout period 703*a* and/or the second set of imaging data (e.g., imaging data 720*b*) obtained during the second readout period 703*b*. The scheme in FIGS. 7A and 7B involves a series of two-image rotations. In each two-image rotation, two sets of imaging data (e.g., imaging data 720*a* and 720*b*) are acquired and the next two-image rotation starts. In FIG. 7B, the first readout period 703*a* and the second readout period 703*b*, taken together, form a two-frame image acquisition rotation. Multiple image acquisition rotations can be performed when imaging the tissue of the subject (i.e., these steps can be repeated).

Figure 7C:
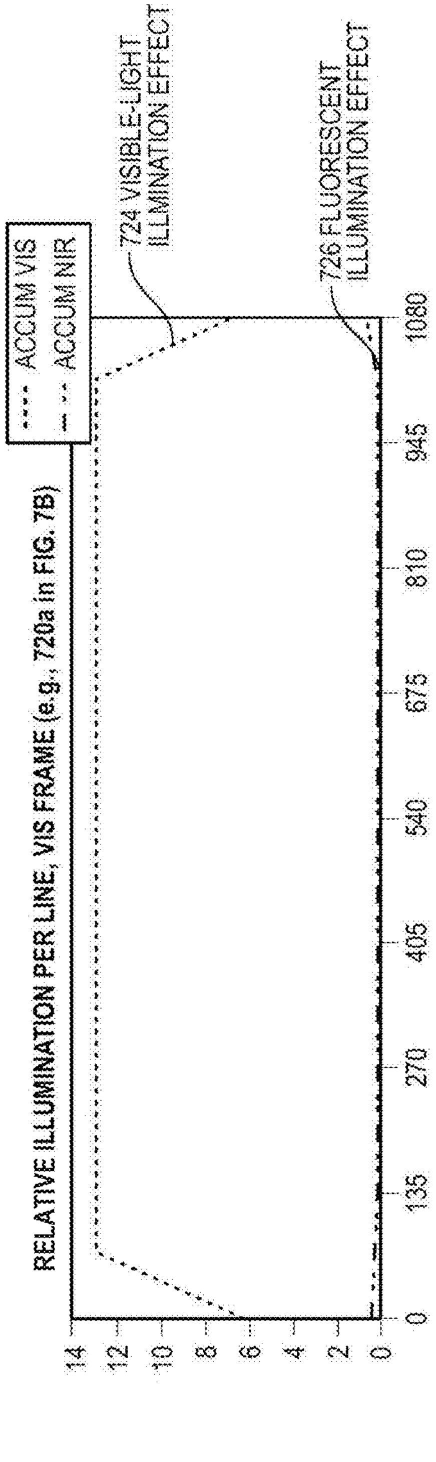
FIG. 7C illustrates the relative effect of each illumination source on a visible-light image frame, in accordance with some examples.
Figure 7D:
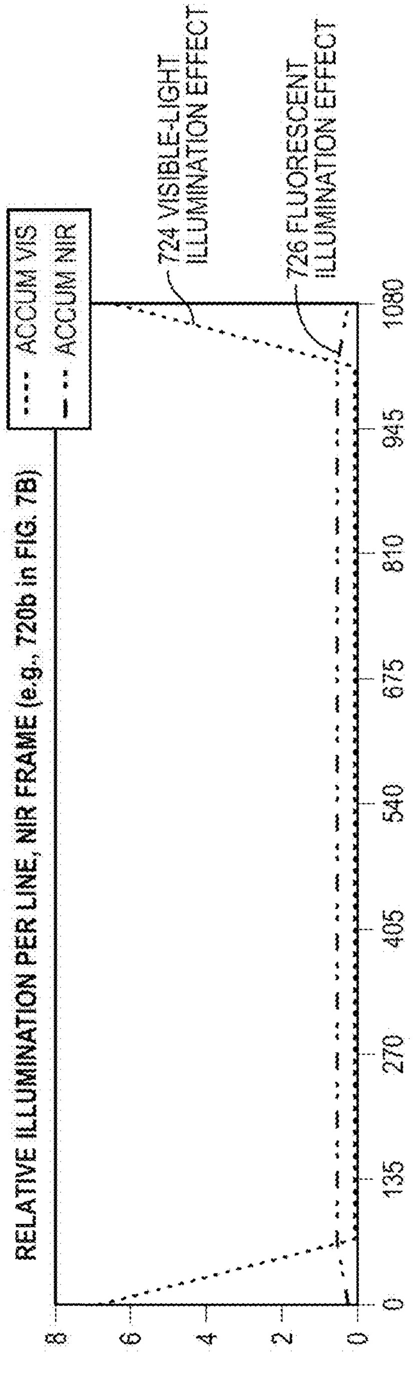
FIG. 7D illustrates the relative effect of each illumination source on a fluorescence image frame, in accordance with some examples.

FIGS. 7C and 7D illustrate the effects of the visible-light illumination source and the fluorescence excitation illumination source on each line of an image frame, in accordance with some examples. For each image frame, lines range from line 0 to line 1080, as shown by the x-axis of each figure. In some examples, line 0 can correspond to the top line of pixels of the image frame. Line 1080 can correspond to the bottom line of pixels of the image frame. Although the depicted example assumes that the rolling shutter imager is a 1080-line HD image sensor, the imaging can also be performed on higher or lower resolution image sensors. In FIGS. 7C and 7D, the y-axis represents the amount of effect of each illumination source. The effect 724 indicates, for each line of the image frame, the amount of effect from light reflected from illumination of a tissue of the subject by the visible-light illumination source. The effect 726 indicates, for each line of the image frame, the amount of effect from fluorescence light emitted due to illumination of a tissue of the subject by the fluorescence excitation illumination source.

FIG. 7C illustrates the relative effect of each illumination source on a visible-light image frame, which may correspond to imaging data 720*a* in FIG. 7B. In the visible-light image frame, light reflected from illumination of a tissue of the subject by the visible-light illumination source reaches the rolling shutter imager, affecting each line of the visible-light image frame as shown by effect 724. In the depicted example, the effect 724 ranges between a value of 6-13 (generally 13 for most of the lines 0-1080). The effect 726 of the fluorescence excitation illumination source remains below a value of 1 (generally 0 for most of the lines) due to the fluorescence excitation illumination source being off for this visible-light image frame. As shown, the effect 726 of the fluorescence excitation illumination source on the visible-light image frame is relatively small compared to the effect 724 of the visible-light illumination source.

FIG. 7D illustrates the relative effect of each illumination source on a fluorescence image frame, which may correspond to imaging data 720*b* in FIG. 7B. Unlike the visible-light image frame of FIG. 7C, in the fluorescence image frame, reflected visible-light illumination is blocked by the light shutter for most of the lines. The effect 724 indicates relatively low values for the first few and last few lines of the image frame and 0 for the remaining lines. In comparison, light due to illumination of a tissue of the subject by the fluorescence excitation illumination source reaches the rolling shutter imager, affecting each line of the visible-light image frame as shown by effect 726. The effect 726 of the fluorescence excitation illumination source indicates relatively low values for the first few and last few lines of the image frame and slightly below 1 for the remaining lines. This is a lower value than the value of effect 626, which has a constant value of 3. Accordingly, compared to imaging systems with longer pulses or a constant level of fluorescence excitation illumination, the imaging systems of FIGS.

7A-7D that utilize shorter and less frequent pulses of fluorescence excitation illumination can produce image frames associated with reduced fluorescence excitation strength.

In FIGS. 7C and 7D, the effect 724 of the visible-light illumination source and the effect 726 of the fluorescence excitation illumination source can pollute the first 71 lines and last 68 lines of each image frame. The exact number of polluted lines can depend on the on-period for the sources. The polluted lines are denoted by the diagonal portions of the effect 724 and the effect 726 near line 0 and line 1080 (e.g., the first 71 lines and the last 68 lines) and can produce visual artifacts upon the generation of the image frame. Accordingly, the polluted lines can be trimmed off in processing (e.g., the top and bottom of each image frame can be masked to remove the resulting artifacts).

Example Three of the Illumination Scheme

Figure 8A:
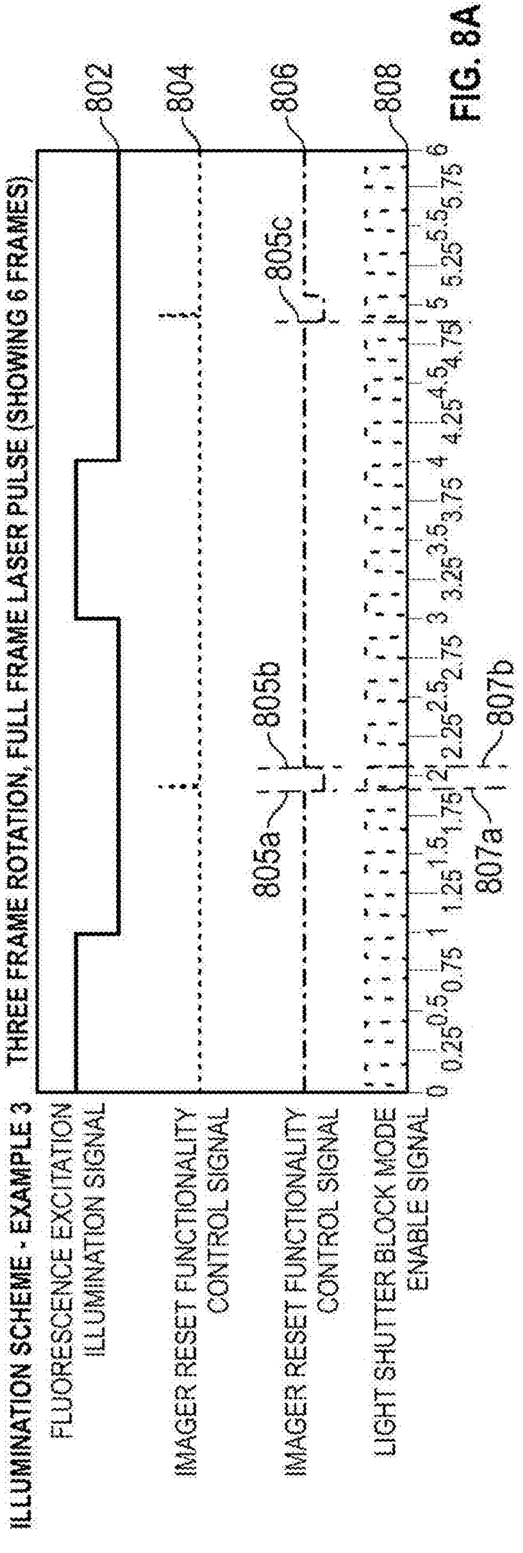
FIG. 8A illustrates exemplary operations of an exemplary imaging system, in accordance with some examples.
Figure 8B:
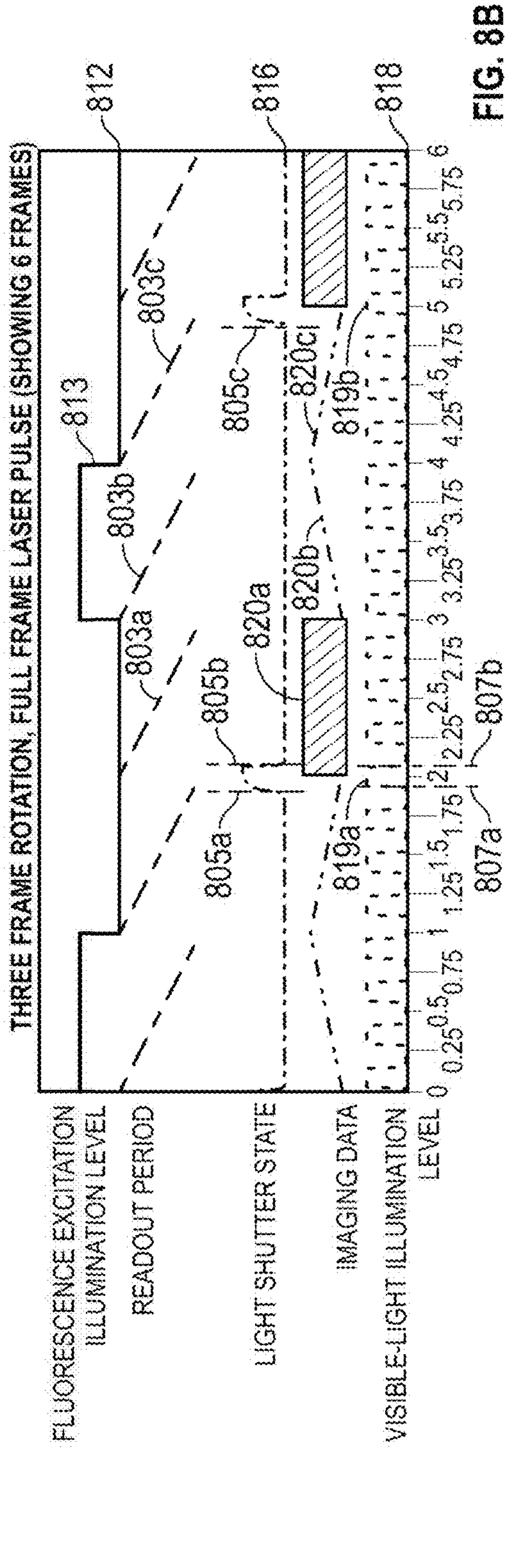
FIG. 8B illustrates a timing diagram of the exemplary imaging system, in accordance with some examples.

FIGS. 8A and 8B illustrate timing diagrams for operating an imaging system for imaging tissue from a subject, in accordance with some examples. The imaging system includes a rolling shutter imager, a fluorescence excitation illumination source, and a visible-light illumination source, and a light shutter. The fluorescence excitation illumination source of the imaging system is set to be modulated (i.e., pulsed). However, unlike the imaging system of FIGS. 6A and 6B, which involves a series of two-image rotations, the illumination scheme in FIGS. 8A and 8B involves a series of three-image rotations. Three sets of imaging data (e.g., imaging data 820*a*, 820*b*, and 820*c* in FIG. 8B) are acquired in each three-image rotation, and subsequently the next three-image rotation starts. In the depicted example, each three-image rotation results in a visible-light image frame (e.g., imaging data 820*a*) corresponding to a first readout period (e.g., readout period 803*a*), followed by a first fluorescence image frame (e.g., imaging data 820*b*) corresponding to a second readout period (e.g., readout period 803*b*), then followed by a second fluorescence image frame (e.g., imaging data 820*c*) corresponding to a third readout period (e.g., readout period 803*c*). The fluorescence excitation illumination source is on (e.g., fluorescence excitation illumination pulse 813 in FIG. 8B) for the entire duration of the second readout period (e.g., 803*b* in FIG. 8B) and is otherwise off during the three-image rotation. The illumination scheme results in the lines (i.e., rows of pixels) in the first fluorescence image frame 820*b* gradually increase fluorescence level data from zero fluorescence in the first line to a full frame-period of fluorescence in the last line. The illumination scheme further results in the lines (i.e., rows of pixels) in the second fluorescence image frame 820*c* gradually decreasing in fluorescence level from a full frame-period of fluorescence in the first line to zero fluorescence in the last line. The two fluorescence frames can be summed to produce an image with equal corresponding fluorescence excitation illumination for every line.

Producing images by using a series of three-image rotations provide a number of technical advantages. For example, the three-image rotation scheme of FIGS. 8A and 8B allows for more excitation power to be used on the first fluorescence image frame while remaining below the maximum instantaneous fluorescence exposure. Additionally, pulsing the fluorescence excitation illumination source on for only one of the two fluorescence image frames (i.e., only during the second readout period 803*b*) is energy-efficient because all or substantially all of the fluorescence excitation illumination is used for imaging. By pulsing the fluorescence excitation illumination source on for only one of the two fluorescence image frames, the same image quality can be achieved with less optical energy, less tissue heating, and less of the photo-bleaching effect than would be possible with pulsing the fluorescence excitation illumination source for both image frames. Furthermore, not providing fluorescence excitation illumination during visible-light illumination frames eliminates the need to correct for fluorescence in those frames. In some examples, the longer rotation (three-image vs. two-image) can reduce the output image update rate to ⅔ of the standard rate (e.g., to 40 Hz instead of the standard 60 Hz). This drawback can be eliminated by running the sensor of the rolling shutter imager at 180 Hz instead of 120 Hz, and scaling all of the illumination timing accordingly.

FIG. 8A illustrates control signals for operating various components of the imaging system, in accordance with some examples. Specifically, FIG. 8A illustrates a control signal 802 for operating the fluorescence excitation illumination source, a control signal 804 for operating a reset functionality of the rolling shutter imager, a control signal 806 for operating the light shutter, and a control signal 808 for operating the visible-light illumination source.

With reference to FIG. 8A, the control signal 802 for operating the fluorescence excitation illumination source is modulated. Specifically, the control signal 802 comprises a sequence of control signal pulses. Each control signal pulse of the control signal 802 can cause the fluorescence excitation illumination source to be activated and to provide a fluorescence excitation illumination pulse for the duration of the pulse width. In the depicted example, one pulse of the control signal 802, shown as 813, can occur per image acquisition rotation during the second readout period (shown as 803*b*) of the three readout periods forming the imaging acquisition rotation. In the depicted example, the frequency of the control signal 802 for operating the fluorescence excitation illumination source is 40 Hz. The frequency and pulse width are constrained by the need to run the fluorescence excitation illumination source at a high enough instantaneous power for a short pulse duration to be sufficient for the desired fluorescence response, while remaining within optical safety limits for instantaneous power. A longer pulse width can be employed at the expense of trimming more lines from the top and bottom of the processed image.

Further with reference to FIG. 8A, the control signal 808 for operating the visible-light illumination source is modulated. Specifically, the control signal 808 comprises a sequence of control signal pulses. Each control signal pulse of the control signal 808 can cause the visible-light illumination source to be activated and to generate a visible-light illumination pulse for the duration of the pulse width. In the depicted example, the frequency of the control signal 808 for operating the visible-light illumination source is 440 Hz.

Further with reference to FIG. 8A, the control signal 806 for operating the light shutter controls the timing for transitioning the light shutter between the closed state and the open state. In the depicted example, the control signal 806 dictates when to enable a "block mode" (i.e., the closed state) of the light shutter. At any given time, the control signal 806 can be either high (indicating that the "block mode" is enabled) or low (indicating that the "block mode" is disabled).

At time 805*a*, the control signal 806 for operating the light shutter changes from high (i.e., block mode enabled) to low (i.e., block mode disabled) to cause the light shutter to transition from the closed state to the open state. Then at time 805*b*, the control signal 806 for operating the light shutter changes from low (i.e., block mode disabled) to high (i.e., block mode enabled) to cause the light shutter to transition from the open state to the closed state. As discussed in more detail in FIG. 8B, the disabling of the block mode of the light shutter (between the time 805*a* and the time 805*b*) causes the light shutter to allow the passage of light reflected from illumination of the tissue of the subject with the visible-light illumination pulse (generated by the control signal 808 between the time 807*a* and the time 807*b*). Further, regardless of the state of the light shutter, the light shutter always allows the passage of the light emitted due to illumination of the tissue of the subject with the fluorescence excitation illumination source (generated by the control signal 802). In fact, in the depicted example, the time periods in which the fluorescence excitation illumination source is on occur only when the light shutter is in the closed state, yet light emitted due to illumination of the tissue of the subject with the fluorescence excitation illumination source (generated by the control signal 802) is not blocked by the light shutter.

FIG. 8B illustrates a timing diagram for generating imaging data by operating an imaging system based on the control signals depicted in FIG. 8A, in accordance with some examples. The x-axis (i.e., time) of the timing diagram in FIG. 8A is aligned with the x-axis (i.e., time) of the timing diagram in FIG. 8B. The alignment of the axes illustrates how the control signals in FIG. 8A dictate the illumination level 812 of the fluorescence excitation illumination source over time, the illumination level 818 of the visible-light illumination source over time, the state 816 of the light shutter over time, the readout periods 803*a-c*, and the generation of imaging data 820*a-c* in FIG. 8B.

With reference to FIG. 8B, the illumination level 812 of the fluorescence excitation illumination source is shown to comprise a sequence of fluorescence excitation illumination pulses. This is because the control signal 802 for operating the fluorescence excitation illumination source in FIG. 8A comprises a sequence of control signal pulses. As discussed above, each control signal pulse of the control signal 802 can cause the fluorescence excitation illumination source to be activated and to provide a fluorescence excitation illumination pulse for the duration of the pulse width. Accordingly, the control signal 802 for operating the visible-light illumination source generates a sequence of fluorescence excitation illumination pulses (e.g., fluorescence excitation illumination pulse 813), as illustrated by the illumination level 812. In some examples, at least part of the fluorescence excitation illumination pulse 813 can occur during the collection of imaging data for a first fluorescence image frame of the three-frame rotation.

Further with reference to FIG. 8B, the illumination level 818 of the visible-light illumination source is shown to comprise a sequence of visible-light illumination pulses. This is because the control signal 808 for operating the visible-light illumination source in FIG. 8A comprises a sequence of control signal pulses. As discussed above, each control signal pulse of the control signal 808 can cause the visible-light illumination source to be activated and to generate a visible-light illumination pulse for the duration of the pulse width. Accordingly, the control signal 808 for operating the visible-light illumination source in FIG. 8A generates a sequence of visible-light illumination pulses 818 in FIG. 8B.

Further with reference to FIG. 8B, the light shutter state 816 shows that the light shutter is generally in the closed state but is transitioned into the open state periodically in accordance with the control signal 806 for operating the light shutter in FIG. 8A. For example, at time 805*a*, the light shutter starts to transition from the closed state to the open state in accordance with the control signal 806 for operating the light shutter at the time 805*a* in FIG. 8A. Further, at time 805*b*, the light shutter starts to transition from the open state to the closed state in accordance with the control signal 806 for operating the light shutter at the time 805*b* in FIG. 8A. Between the time 805*a* (when the light shutter starts to transition from the closed state to the open state) and the time 805*b* (when the light shutter starts to transition from the open state to the closed state), the light shutter allows the passage of light reflected from illumination of the tissue of the subject with the visible-light illumination pulse 819*a*.

The light shutter is controlled by the control signal 806 in FIG. 8A to periodically open (e.g., at 805*a*, at 805*c*), each time to allow the reflected light from illumination of the tissue of the subject with a single visible-light illumination pulse (e.g., 819*a*, 819*b*) to pass through the light shutter and reach the rolling shutter imager. These visible-light illumination pulses (e.g., 819*a*, 819*b*) are referred to as “primary” visible-light illumination pulses. Between two neighboring primary visible-light illumination pulses, there can be one or more “compensating” visible-light illumination pulses. In the depicted example, between two neighboring primary visible-light illumination pulses (e.g., 819*a* and 819*b*), there are ten compensating visible-light illumination pulses, such that the frequency of the control signal 808 for operating the visible-light illumination source is 440 Hz. The minimum number of compensating visible-light illumination pulses between two neighboring primary visible-light illumination pulses is one pulse, such that the frequency of the control signal 808 for operating the visible-light illumination source is 80 Hz. The maximum number of compensating visible-light illumination pulses is bounded by the off period between the pulses needing to be longer than the ramp-open time of the light shutter, and the on period of each pulse needing to be long enough to acquire a reasonably bright image.

As shown in FIG. 8B, the light shutter is in a closed state during the compensating visible-light illumination pulses, thus preventing the reflected light from illumination of the tissue of the subject with the compensating visible-light illumination pulses from passing through the light shutter to reach the rolling shutter imager. However, the light shutter being in the closed state does not prevent light emitted due to illumination of the tissue of the subject with the fluorescence excitation illumination source (generated by the control signal 802) from passing through the light shutter to reach the rolling shutter imager. In fact, in the depicted example, the fluorescence excitation illumination source is on (as shown by the fluorescence excitation illumination pulse 813 of the fluorescence excitation illumination source), and, as such, the fluorescence light due to illumination of the tissue with the fluorescence excitation illumination occurs only when the light shutter is in the closed state. The primary visible-light pulses (e.g., 819*a* and 819*b*) may occur on every third frame, such that they do not fall on the same frame as the fluorescence excitation illumination pulses (e.g., 813).

FIG. 8B further illustrates a series of readout periods (e.g., readout period 803*a*, 803*b*, and 803*c*) and the resulting imaging data (e.g., imaging data 820*a*, 820*b*, and 820*c*). As discussed above, the light shutter starts to transition from the closed state to the open state at the time 805*a* to allow light reflected from illumination of the tissue of the subject with the primary visible-light illumination pulse 819*a* of the pulsed visible-light illumination source to reach the rolling shutter image and to cause accumulation of charge at a plurality of rows of pixels of the rolling shutter imager. The light shutter then transitions to the closed state at the time 805*b* to block the rolling shutter imager from receiving light reflected from illumination of the tissue of the subject with one or more compensating visible-light illumination pulses of the pulsed visible-light illumination source after the primary visible-light illumination pulse 819*a*.

During the readout period 803*a*, the system sequentially reads a first set of accumulated charge at the plurality of rows of pixels from a first row to a last row of the plurality of rows to produce a first set of imaging data 820*a*. The readout period 803*a* is illustrated as a diagonal line in FIG. 8B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially.

The imaging data 820*a* obtained during the readout period 803*a* contains data resulting from the visible-light illumination. The light shutter is open to allow passage of light reflected from illumination of the tissue of the subject with the primary visible-light illumination pulse 819*a* to reach the rolling shutter imager. The fluorescence excitation illumination source is not on (as illustrated by illumination level 812 of the fluorescence excitation illumination source). Accordingly, the plurality of rows of pixels of the rolling shutter imager receive reflected illumination from only the primary visible-light illumination pulse 819*a* for all the lines. Thus, the imaging data 820*a* contains only reflected visible-light illumination data and ambient light imaging data (which is negligible in the combined data due to the dominating visible-light imaging data).

At the end of the readout period 803*a*, the accumulated charge at the plurality of rows can be cleared. As shown in FIG. 8B, the light shutter remains in the closed state after the accumulated charge at the plurality of rows can be cleared at the end of the readout period 803*a* and throughout the readout period 803*b* and most of the readout period 803*c*. After the accumulated charge at the plurality of rows is cleared at the end of the readout period 803*a*, the tissue of the subject is not illuminated with the visible-light illumination source due to the closed shutter but begins to be illuminated by the fluorescence excitation illumination source with the fluorescence illumination pulse 813. The start of the fluorescence excitation illumination pulse 813 is aligned with the start of the readout period 803*b* such that the start of the visible-light illumination pulse 813 aligns with the value of the x-axis (i.e., time) corresponding to the start of the readout period 803*b*.

During the readout period 803*b*, the system sequentially reads a second set of accumulated charge from the first row to the last row of the plurality of rows of pixels to produce a second set of imaging data 820*b*. The readout period 803*b* is also illustrated as a diagonal line in FIG. 8B. In the depicted example, the plurality of rows of pixels of the rolling shutter imager receive fluorescence light due to illumination of the tissue by only the fluorescence excitation illumination pulse 813. During the readout period 803*b*, the first row of pixels of the rolling shutter imager receives zero reflected illumination from the fluorescence excitation illumination pulse 813, while the last row of pixels receives a full frame-period of reflected illumination from the fluorescence excitation illumination pulse 813.

The imaging data 820*b* obtained during the readout period 803*b* contains data resulting from the fluorescence emission and not from the visible-light illumination. Because the light shutter is closed before the end of the readout period 803*a* and throughout the readout period 803*b*, light reflected from illumination of the tissue of the subject by the visible-light illumination source (in this case, the compensating visible-light illumination pulses following the primary visible-light illumination pulse 819*a*) are blocked from reaching the rolling shutter imager. However, because the fluorescence excitation illumination pulse 813 occurs at the start of the readout period 803*b*, light emitted due to illumination of the tissue of the subject by the fluorescence excitation illumination source passes through the closed light shutter and reaches the rolling shutter imager. Accordingly, the imaging data 820*b* contains only fluorescence data.

The ending of the pulse 813 is aligned with the end of the readout period 803*b*. The readout period 803*c* can begin immediately following the end of the readout period 803*b*. During the readout period 803*c*, the system sequentially reads a third set of accumulated charge from the first row to the last row of the plurality of rows of pixels to produce a third set of imaging data 820*c*. The readout period 803*c* is also illustrated as a diagonal line in FIG. 8B. The imaging data 820*c* obtained during the readout period 803*c* contains data collected when the fluorescence excitation illumination source is off (i.e., after the end of the fluorescence excitation illumination pulse 813). During the readout period 803*c*, the first row of pixels of the rolling shutter imager receives a full frame-period of fluorescence light due to illumination of the tissue with the fluorescence excitation illumination pulse 813, while the last row of pixels receives zero fluorescence due to illumination from the fluorescence excitation illumination pulse 813.

Further with reference to FIG. 8B, the imaging system can generate one or more image frames based on the first set of imaging data (e.g., imaging data 820*a*) obtained during the first readout period 803*a*, the second set of imaging data (e.g., imaging data 820*b*) obtained during the second readout period 803*b*, and/or the third set of imaging data (e.g., imaging data 820*c*) obtained during the third readout period 803*c*. As described above, the scheme in FIGS. 8A and 8B involves a series of three-image rotations. Three sets of imaging data (e.g., imaging data 820*a*, 820*b*, and 820*c*) are acquired in each three-image rotation, and subsequently the next three-image rotation starts. In FIG. 8B, the first readout period 803*a*, the second readout period 803*b*, and the third readout period 803*c*, taken together, form a three-frame image acquisition rotation. Multiple image acquisition rotations can be performed when imaging the tissue of the subject (i.e., these steps can be repeated).

In the depicted example, the imaging system can generate a visible-light image frame based on the first set of imaging data. The imaging system can generate a fluorescence image frame based on the second and third sets of imaging data by adding them together during processing. Another type of image frame can be a blended image frame based on both the fluorescence image frames and the visible-light image frame. In some examples, the fluorescence image frames can be overlaid on the visible-light image frame in the blended image frame. In some examples, the blended image frame can be derived from colorizing the visible-light image frame based on the fluorescence image frames (e.g., based on the ratio of the fluorescence image frame to one or more channels of the visible-light frame). The generated image frames can be added to a video stream and displayed on a display to a user (e.g., a medical practitioner such as a surgeon).

Figure 8C:
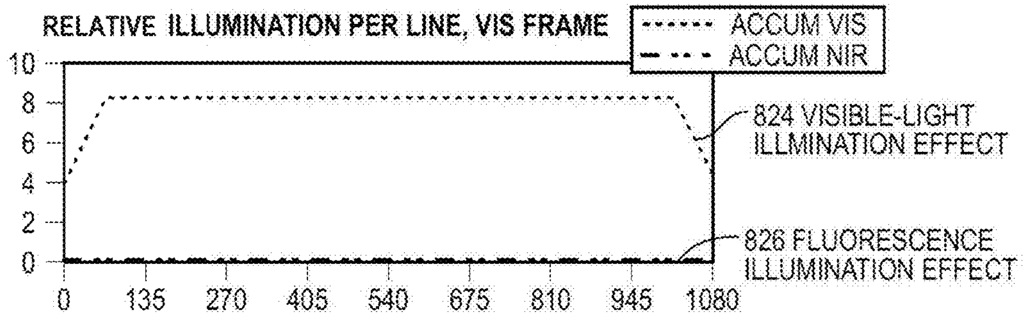
FIG. 8C illustrates the relative effect of each illumination source on a visible-light image frame, in accordance with some examples.
Figure 8D:
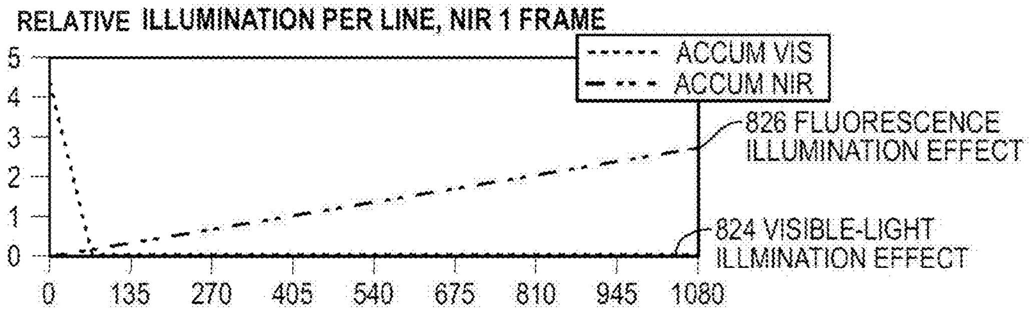
FIG. 8D illustrates the relative effect of each illumination source on a fluorescence image frame, in accordance with some examples.
Figure 8E:
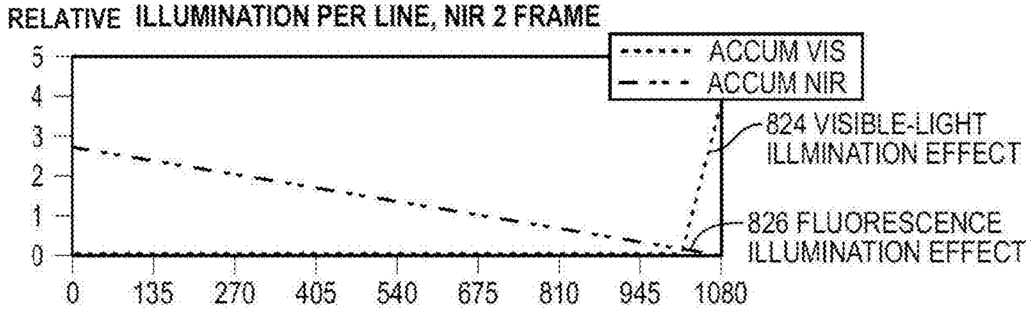
FIG. 8E illustrates the relative effect of each illumination source on a fluorescence image frame, in accordance with some examples.

FIGS. 8C-E illustrate the effects of the visible-light illumination source and the fluorescence excitation illumination source on each line of an image frame, in accordance with some examples. For each image frame, lines range from line 0 to line 1080, as shown by the x-axis of each figure. In some examples, line 0 can correspond to the top line of pixels of the image frame. Line 1080 can correspond to the bottom line of pixels of the image frame. Although the depicted example assumes that the rolling shutter imager is a 1080-line HD image sensor, the imaging can also be performed on higher or lower resolution image sensors. In FIGS. 8C-E, the y-axis represents the amount of effect of each illumination source. The effect 824 indicates, for each line of the image frame, the amount of effect from light reflected from illumination of a tissue of the subject by the visible-light illumination source. The effect 826 indicates, for each line of the image frame, the amount of effect from light emitted due to illumination of a tissue of the subject by the fluorescence excitation illumination source.

FIG. 8C illustrates the relative effect of each illumination source on a visible-light image frame, which may correspond to imaging data 820*a* in FIG. 8B. In the visible-light image frame, light reflected from illumination of a tissue of the subject by the visible-light illumination source reaches the rolling shutter imager, affecting each line of the visible-light image frame as shown by effect 824. In the depicted example, the effect 824 ranges between a value of 4-8 (generally 8 for most of the lines). The effect 826 of the fluorescence excitation illumination source remains at 0 for all of the lines 0-1080 due to the fluorescence excitation illumination source being off for this visible-light image frame.

FIG. 8D illustrates the relative effect of each illumination source on a first fluorescence image frame, which may correspond to imaging data 820*b* in FIG. 8B. Unlike the visible-light image frame of FIG. 8C, in the first fluorescence image frame, reflected visible-light illumination is blocked by the light shutter for most of the lines. The effect 824 indicates relatively high values for the first few lines of the image frame rapidly decreasing to 0 for the remaining lines. In comparison, light due to illumination of a tissue of the subject by the fluorescence excitation illumination source reaches the rolling shutter imager throughout the frame exposure period, affecting each line of the visible-light image frame as shown by effect 826. The effect 826 of the fluorescence excitation illumination source indicates a value of 0 for the first line of the image frame and steadily increases in magnitude until reaching a high relative value of around 3 for the last line of the image frame. The effect 826 of the fluorescence excitation illumination source on the first fluorescence image frame increases toward the later lines due to the rolling nature of the shutter, which begins by reading the first line of the image frame at the beginning of the fluorescence excitation illumination pulse, and finishes by reading the last line of the image frame once it has been exposed to the entire duration of the fluorescence excitation illumination pulse.

FIG. 8E illustrates the relative effect of each illumination source on a second fluorescence image frame, which may correspond to imaging data 820*c* in FIG. 8B. Like the first fluorescence image frame of FIG. 8D, in the second fluorescence image frame, reflected visible-light illumination is blocked by the light shutter for most of the lines (the effect 824 indicates a rapid increase to relatively high values over the last few lines of the image frame and 0 for the previous lines). Light due to illumination of a tissue of the subject by the fluorescence excitation illumination source reaches the rolling shutter imager throughout the frame exposure period, affecting each line of the visible-light image frame as shown by effect 826. However, unlike the first fluorescence image frame of FIG. 8D, for the second fluorescence image frame, the fluorescence excitation illumination source is turned off such that no fluorescence excitation illumination is provided during the corresponding frame readout period 803*c*. The effect 826 of the fluorescence excitation illumination source indicates high values for the first few lines of the image frame and steadily decreases in magnitude until reaching 0 for the last line of the image frame. The effect 826 of the fluorescence excitation illumination source on the first fluorescence image frame decreases toward the later lines due to the rolling nature of the shutter, which begins by reading the first line of the image frame at the end of the fluorescence excitation illumination pulse, and finishes by reading the last line of the image frame once that line has not been exposed to fluorescence excitation illumination for the entire duration of the readout period (e.g., readout period 803*c* of FIG. 8B).

In FIGS. 8C-E, the effect 824 of the visible-light illumination source can pollute the first and/or last few lines of each image frame. The exact number of polluted lines can depend on the on-period for the source. The polluted lines are denoted by the diagonal portions of the effect 824 near line 0 and line 1080 and can produce visual artifacts upon the generation of the image frame. Accordingly, the polluted lines can be trimmed off in processing (e.g., the top and bottom of each image frame can be masked to remove the resulting artifacts).

Example Four of the Illumination Scheme

Figure 9A:
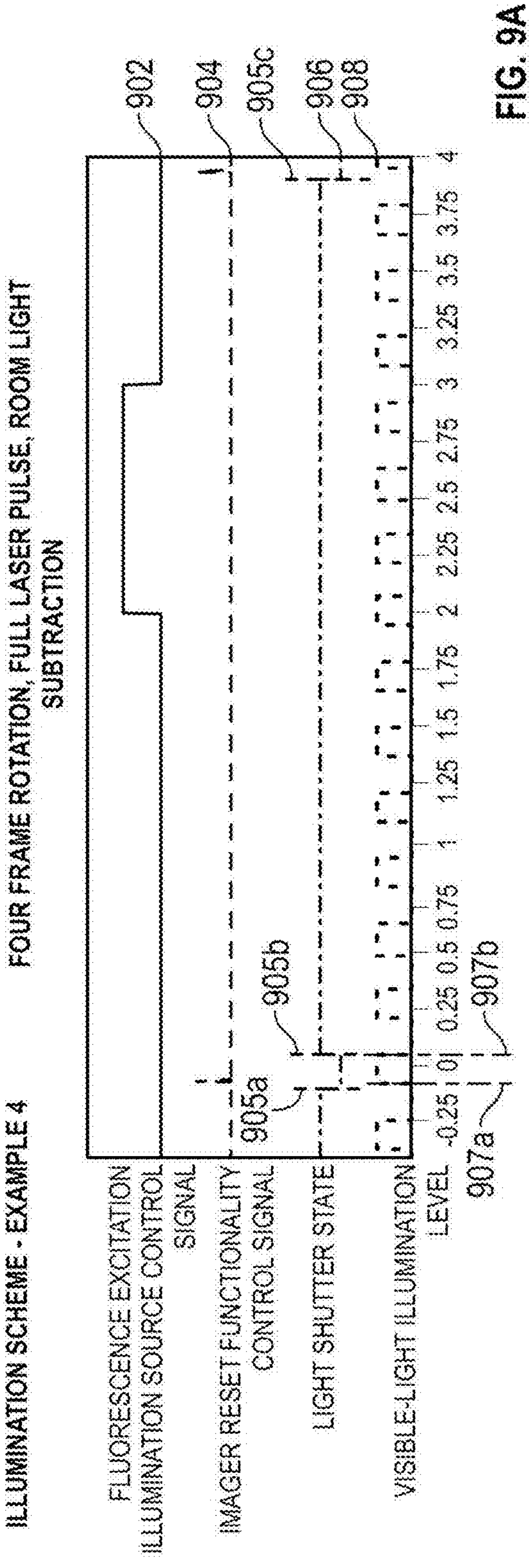
FIG. 9A illustrates exemplary operations of an exemplary imaging system, in accordance with some examples.
Figure 9B:
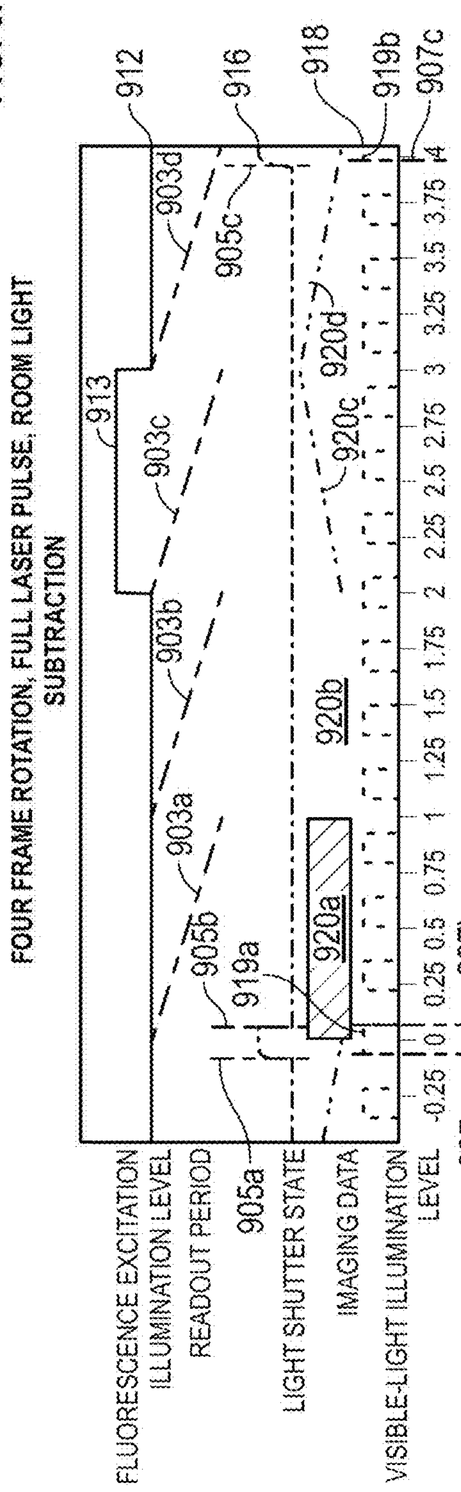
FIG. 9B illustrates a timing diagram of the exemplary imaging system, in accordance with some examples.

FIGS. 9A and 9B illustrate timing diagrams for operating an imaging system for imaging tissue from a subject, in accordance with some examples. The imaging system includes a rolling shutter imager, a fluorescence excitation illumination source, and a visible-light illumination source, and a light shutter. The fluorescence excitation illumination source of the imaging system is set to be modulated (i.e., pulsed). The scheme in FIGS. 9A and 9B involves a series of four-image rotations. Four sets of imaging data (e.g., imaging data 920*a*, 920*b*, 920*c*, and 920*d* in FIG. 9B) are acquired in each four-image rotation, and subsequently the next four-image rotation starts. In the depicted example, the acquired imaging data includes a visible-light image frame, followed by an ambient light image frame, then followed by a first fluorescence image frame, then followed by a second fluorescence image frame. The two fluorescence image frames can be summed in processing to produce an image with equal corresponding fluorescence excitation illumination for every line. The ambient light image frame can then be subtracted from the aggregated two fluorescence image frames in processing to correct for the effects of ambient light.

In the depicted example, producing images by using a series of four-image rotations has several advantages. For instance, the four-image rotation scheme of FIGS. 9A and 9B allows for ambient light subtraction to be performed, thereby correcting for any pollution from ambient light. In some examples, the longer rotation (four-image vs. three-image) may reduce the output image update rate by ¾ (e.g., 30 Hz for a four-image rotation instead of 40 Hz for a three-image rotation). However, this potential drawback can be eliminated by running the sensor of the rolling shutter imager at a faster rate (e.g., 240 Hz), and scaling all of the illumination timing accordingly.

FIG. 9A illustrates control signals for operating various components of the imaging system, in accordance with some examples. Specifically, FIG. 9A illustrates a control signal 902 for operating the fluorescence excitation illumination source, a control signal 904 for operating a reset functionality of the rolling shutter imager, a control signal 906 for operating the light shutter, and a control signal 908 for operating the visible-light illumination source.

With reference to FIG. 9A, the control signal 902 for operating the fluorescence excitation illumination source is modulated. Specifically, the control signal 902 comprises a sequence of control signal pulses. Each control signal pulse of the control signal 902 can cause the fluorescence excitation illumination source to be activated and to provide a fluorescence excitation illumination pulse for the duration of the pulse width. In the depicted example, one pulse of the control signal 902 can occur per image acquisition rotation, such that the fluorescence excitation illumination source is activated to produce one illumination pulse (e.g., pulse 913 in FIG. 9B) during an image acquisition rotation. For example, the fluorescence excitation illumination source can be activated for the third readout period of the four readout periods. In the depicted example, the frequency of the control signal 902 for operating the fluorescence excitation illumination source is 30 Hz. The frequency and pulse width are constrained by the need to run the fluorescence excitation illumination source at a high enough instantaneous power for a short pulse duration to be sufficient for the desired fluorescence response, while remaining within optical safety limits for instantaneous power. A longer pulse width can be employed at the expense of trimming more lines from the top and bottom of the processed image.

Further with reference to FIG. 9A, the control signal 908 for operating the visible-light illumination source is modulated. Specifically, the control signal 908 comprises a sequence of control signal pulses. Each control signal pulse of the control signal 908 can cause the visible-light illumination source to be activated and to generate a visible-light illumination pulse for the duration of the pulse width. In the depicted example, the frequency of the control signal 908 for operating the visible-light illumination source is 420 Hz.

Further with reference to FIG. 9A, the control signal 906 for operating the light shutter controls the timing for transitioning the light shutter between the closed state and the open state. In the depicted example, the control signal 906 dictates when to enable a “block mode” (i.e., the closed state) of the light shutter. At any given time, the control signal 906 can be either high (indicating that the “block mode” is enabled) or low (indicating that the “block mode” is disabled).

At time 905*a*, the control signal 906 for operating the light shutter changes from high (i.e., block mode enabled) to low (i.e., block mode disabled) to cause the light shutter to transition from the closed state to the open state. Then at time 905*b*, the control signal 906 for operating the light shutter changes from low (i.e., block mode disabled) to high (i.e., block mode enabled) to cause the light shutter to transition from the open state to the closed state. As discussed in more detail in FIG. 9B, the disabling of the block mode of the light shutter (between the time 905*a* and the time 905*b*) causes the light shutter to allow the passage of light reflected from illumination of the tissue of the subject with the visible-light illumination pulse (generated by the control signal 908 between the time 907*a* and the time 907*b*). Further, regardless of the state of the light shutter, the light shutter always allows the passage of the light emitted due to illumination of the tissue of the subject with the fluorescence excitation illumination source (generated by the control signal 902). In fact, in the depicted example, the time periods in which the fluorescence excitation illumination source is on occur only when the light shutter is in the closed state, yet light emitted due to illumination of the tissue of the subject with the fluorescence excitation illumination source (generated by the control signal 902) is not blocked by the light shutter.

FIG. 9B illustrates a timing diagram for generating imaging data by operating an imaging system based on the control signals depicted in FIG. 9A, in accordance with some examples. The x-axis (i.e., time) of the timing diagram in FIG. 9A is aligned with the x-axis (i.e., time) of the timing diagram in FIG. 9B. The alignment of the axes illustrates how the control signals in FIG. 9A dictate the illumination level 912 of the fluorescence excitation illumination source over time, the illumination level 918 of the visible-light illumination source over time, the state 916 of the light shutter over time, the readout periods 903*a-d*, and the generation of imaging data 920*a-d* in FIG. 9B.

With reference to FIG. 9B, the illumination level 912 of the fluorescence excitation illumination source is shown to comprise a sequence of fluorescence excitation illumination pulses. This is because the control signal 902 for operating the fluorescence excitation illumination source in FIG. 9A comprises a sequence of control signal pulses. As discussed above, each control signal pulse of the control signal 902 can cause the fluorescence excitation illumination source to be activated and to provide a fluorescence excitation illumination pulse for the duration of the pulse width. Accordingly, the control signal 902 for operating the visible-light illumination source generates a sequence of fluorescence excitation illumination pulses (e.g., fluorescence excitation illumination pulse 913), as illustrated by the illumination level 912. In the depicted example, the fluorescence excitation illumination pulse 913 can occur during the third readout period 903*c* of the four-image rotation.

Further with reference to FIG. 9B, the illumination level 918 of the visible-light illumination source is shown to comprise a sequence of visible-light illumination pulses. This is because the control signal 908 for operating the visible-light illumination source in FIG. 9A comprises a sequence of control signal pulses. As discussed above, each control signal pulse of the control signal 908 can cause the visible-light illumination source to be activated and to generate a visible-light illumination pulse for the duration of the pulse width. Accordingly, the control signal 908 for operating the visible-light illumination source in FIG. 9A generates a sequence of visible-light illumination pulses 918 in FIG. 9B.

Further with reference to FIG. 9B, the light shutter state 916 shows that the light shutter is generally in the closed state but is transitioned into the open state periodically in accordance with the control signal 906 for operating the light shutter in FIG. 9A. For example, at time 905*a*, the light shutter starts to transition from the closed state to the open state in accordance with the control signal 906 for operating the light shutter at the time 905*a* in FIG. 9A. Further, at time 905*b*, the light shutter starts to transition from the open state to the closed state in accordance with the control signal 906 for operating the light shutter at the time 905*b* in FIG. 9A. Between the time 905*a* (when the light shutter starts to transition from the closed state to the open state) and the time 905*b* (when the light shutter starts to transition from the open state to the closed state), the light shutter allows the passage of light reflected from illumination of the tissue of the subject with the visible-light illumination pulse 919*a*.

The light shutter is controlled by the control signal 906 in FIG. 9A to periodically open (e.g., at 905*a*, at 905*c*), each time to allow the reflected light from illumination of the tissue of the subject with a single visible-light illumination pulse (e.g., 919*a*, 919*b*) to pass through the light shutter and reach the rolling shutter imager. These visible-light illumination pulses (e.g., 919*a*, 919*b*) are referred to as "primary" visible-light illumination pulses. Between two neighboring primary visible-light illumination pulses, there can be one or more "compensating" visible-light illumination pulses. In the depicted example, between two neighboring primary visible-light illumination pulses (e.g., 919*a* and 919*b*), there are thirteen compensating visible-light illumination pulses, such that the frequency of the control signal 908 for operating the visible-light illumination source is 420 Hz. To ensure that the visible-light illumination appears continuous to the human eye (i.e., for the user's visual comfort), the minimum number of compensating visible-light illumination pulses between two neighboring primary visible-light illumination pulses is two pulses, such that the frequency of the control signal 908 for operating the visible-light illumination source is 90 Hz. The maximum number of compensating visible-light illumination pulses is bounded by the off period between the pulses needing to be longer than the ramp-open time of the light shutter, and the on period of each pulse needing to be long enough to acquire a reasonably bright image.

As shown in FIG. 9B, the light shutter is in a closed state during the compensating visible-light illumination pulses, thus preventing the reflected light from illumination of the tissue of the subject with the compensating visible-light illumination pulses from passing through the light shutter to reach the rolling shutter imager. However, the light shutter being in the closed state does not prevent light emitted due to illumination of the tissue of the subject with the fluorescence excitation illumination source (generated by the control signal 902) from passing through the light shutter to reach the rolling shutter imager. The primary visible-light pulses (e.g., 919*a* and 919*b*) may occur on every fourth frame.

FIG. 9B further illustrates a series of readout periods (e.g., readout period 903*a*, 903*b*, 903*c*, and 903*d*) and the resulting imaging data (e.g., imaging data 920*a*, 920*b*, 920*c*, and 920*d*). As discussed above, the light shutter starts to transition from the closed state to the open state at the time 905*a* to allow light reflected from illumination of the tissue of the subject with the primary visible-light illumination pulse 919*a* of the pulsed visible-light illumination source to reach the rolling shutter image and to cause accumulation of charge at a plurality of rows of pixels of the rolling shutter imager. The light shutter then transitions to the closed state at the time 905*b* to block the rolling shutter imager from receiving light reflected from illumination of the tissue of the subject with one or more compensating visible-light illumination pulses of the pulsed visible-light illumination source after the primary visible-light illumination pulse 919*a*.

During the readout period 903*a*, the system sequentially reads a first set of accumulated charge at the plurality of rows of pixels from a first row to a last row of the plurality of rows to produce a first set of imaging data 920*a*. The readout period 903*a* is illustrated as a diagonal line in FIG. 9B. It should be appreciated by one of ordinary skill in the art that the diagonal line reflects the rolling nature of the rolling shutter architecture, in which the rows of pixels of the rolling shutter imager are read sequentially row-by-row, from the top row to the bottom row of the image frame. Specifically, the y-axis of each readout period line corresponds to the rows of pixels of the rolling shutter imager, and the x-axis corresponds to the time at which each row of pixels is read. The diagonal line indicates that the rows of pixels are read from the top row to the bottom row sequentially.

The imaging data 920*a* obtained during the readout period 903*a* contains data resulting from the visible-light illumination. The light shutter is open to allow passage of light reflected from illumination of the tissue of the subject with the primary visible-light illumination pulse 919*a* to reach the rolling shutter imager. The fluorescence excitation illumination source is not on (as illustrated by illumination level 912 of the fluorescence excitation illumination source). Accordingly, the plurality of rows of pixels of the rolling shutter imager receive reflected illumination from only the primary visible-light illumination pulse 919*a*. Thus, the imaging data 920*a* contains only visible-light illumination data and little to no fluorescence data.

At the end of the readout period 903*a*, the accumulated charge at the plurality of rows can be cleared. As shown in FIG. 9B, the light shutter remains in the closed state after the accumulated charge at the plurality of rows can be cleared at the end of the readout period 903*a* and throughout the readout periods 903*b-c*. After the accumulated charge at the plurality of rows is cleared at the end of the readout period 903*a*, the tissue of the subject is not illuminated with the visible-light illumination source due to the closed shutter and is also not illuminated by the fluorescence excitation illumination source.

During the readout period 903*b*, the system sequentially reads a second set of accumulated charge at the plurality of rows of pixels from a first row to a last row of the plurality of rows to produce a second set of imaging data 920*b*. The readout period 903*b* is also illustrated as a diagonal line in FIG. 9B. The imaging data 920*b* obtained during the readout period 903*b* contains ambient light data. The light shutter is closed to prevent light visible light, including light reflected from illumination of the tissue of the subject by the visible-light illumination source from reaching the rolling shutter imager (as illustrated by light shutter state 916). The fluorescence excitation illumination source is not on (as illustrated by illumination level 912 of the fluorescence excitation illumination source). Accordingly, the plurality of rows of pixels of the rolling shutter imager receive reflected illumination from only the non-visible portion (e.g., infrared portion) of ambient light. Thus, the imaging data 920*a* contains only non-visible ambient light data (from ambient light in the fluorescence emission band). At the end of the readout period 903*b*, the accumulated charge at the plurality of rows can be cleared.

The readout period 903*c* starts immediately after the readout period 903*b*. During the readout period 903*c*, the system sequentially reads a third set of accumulated charge from the first row to the last row of the plurality of rows of pixels to produce a third set of imaging data 920*c*. The readout period 903*c* is also illustrated as a diagonal line in FIG. 9B. In the depicted example, the plurality of rows of pixels of the rolling shutter imager receive reflected illumination from non-visible ambient light and fluorescence light due to illumination of the tissue with the fluorescence excitation illumination pulse 913. During the readout period 903*c*, the fluorescence level of the lines increases progressively, with the first row of pixels of the rolling shutter imager receiving zero reflected illumination from the fluorescence excitation illumination pulse 913, while the last row of pixels receiving a full frame-period of reflected illumination from the fluorescence excitation illumination pulse 913.

The imaging data 920*c* obtained during the readout period 903*c* contains data resulting from the fluorescence excitation illumination and not from the visible-light illumination. Because the light shutter is closed before the end of the readout period 903*a* and throughout the readout periods 903*b-c*, light reflected from illumination of the tissue of the subject by the visible-light illumination source (in this case, the compensating visible-light illumination pulses following the primary visible-light illumination pulse 919*a*) are blocked from reaching the rolling shutter imager. However, because the fluorescence excitation illumination pulse 913 occurs at the start of the readout period 903*c*, the fluorescence excitation illumination source is on during the third readout period 903*c*. Light emitted due to illumination of the tissue of the subject by the fluorescence excitation illumination source passes through the closed light shutter and reaches the rolling shutter imager. Accordingly, the imaging data 920*c* contains only fluorescence data (as well as any contribution from ambient light that is not blocked by the closed light shutter). This fluorescence data is similar to the fluorescence data described in FIG. 8B (e.g., imaging data 820*b*).

The fourth readout period 903*d* occurs immediately after the third readout period 903*d*. During the readout period 903*d*, the system sequentially reads a fourth set of accumulated charge from the first row to the last row of the plurality of rows of pixels to produce a fourth set of imaging data 920*d*. The readout period 903*d* is also illustrated as a diagonal line in FIG. 9B. The imaging data 920*d* obtained during the readout period 903*d* contains data collected when the fluorescence excitation illumination source is off (i.e., after the end of the visible-light illumination pulse 913). During the readout period 903*d*, the first row of pixels of the rolling shutter imager receives a full frame-period of reflected illumination from the fluorescence excitation illumination pulse 913 and the fluorescence level progressively decreases, with the last row of pixels receiving zero reflected illumination from the fluorescence excitation illumination pulse 913 (as well as any contribution from ambient light that is not blocked by the closed light shutter).

Further with reference to FIG. 9B, the imaging system can generate one or more image frames based on the first set of imaging data (e.g., imaging data 920*a*) obtained during the first readout period 903*a*, the second set of imaging data (e.g., imaging data 920*b*) obtained during the second readout period 903*b*, the third set of imaging data (e.g., imaging data 920*c*) obtained during the third readout period 903*c*, and/or the fourth set of imaging data (e.g., imaging data 920*d*) obtained during the fourth readout period 903*d*. As described above, the scheme in FIGS. 9A and 9B involves a series of four-image rotations. Four sets of imaging data (e.g., imaging data 920*a*, 920*b*, 920*c*, and 920*d*) are acquired in each four-image rotation, and subsequently the next four-image rotation starts. In FIG. 9B, the first readout period 903*a*, the second readout period 903*b*, the third readout period 903*c*, and the fourth readout period 903*d*, taken together, form a four-frame image acquisition rotation. Multiple image acquisition rotations can be performed when imaging the tissue of the subject (i.e., these steps can be repeated).

In the depicted example, the imaging system can generate a visible-light image frame based on the first set of imaging data. The imaging system can generate a fluorescence image frame based on the third and fourth sets of imaging data by adding them together during processing. To correct for non-visible ambient light pollution (e.g., ambient light in the fluorescence emission band), the second set of imaging data can be subtracted from the aggregated third and fourth sets of imaging data.

It should be appreciated by one of ordinary skill in the art that the examples described herein are merely exemplary. For example, the order in which the fluorescence image data, the visible-light image data, and/or the ambident fluorescence image data are acquired can be changed. Further, in some examples, the imaging system can be configured to capture only fluorescence images without capturing visible-light images, or capture both types of images but display only fluorescence images. In any of the examples described herein, the techniques described herein can be used for NIR reflectance imaging without fluorescence excitation imaging.

The foregoing description, for the purpose of explanation, has been described with reference to specific examples. However, the illustrative discussions above are not intended to be exhaustive or to limit the invention to the precise forms disclosed. For the purpose of clarity and a concise description, features are described herein as part of the same or separate examples; however, it will be appreciated that the scope of the disclosure includes examples having combinations of all or some of the features described. Many modifications and variations are possible in view of the above teachings. The examples were chosen and described in order to best explain the principles of the techniques and their practical applications. Others skilled in the art are thereby enabled to best utilize the techniques and various examples with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A method of imaging tissue of a subject using an imaging system comprising an imager, a liquid crystal light shutter configurable to be in an open state and a closed state, a fluorescence excitation illumination source, and a visible-light illumination source, the method comprising:

- transitioning the liquid crystal light shutter to the open state to allow reflected light from illumination of the tissue of the subject with the visible-light illumination source to accumulate charge at a plurality of rows of pixels of the imager;
- transitioning the liquid crystal light shutter to the closed state to prevent the imager from receiving visible light;
- during a first readout period, sequentially reading a first set of accumulated charge at the plurality of rows of pixels from a first row to a last row of the plurality of rows to produce a first set of imaging data;
- illuminating the tissue of the subject with the fluorescence excitation illumination source while the liquid crystal light shutter is in the closed state, wherein the visible light is blocked by the liquid crystal light shutter and light emitted due to illumination with the fluorescence excitation light source is passed through the liquid crystal light shutter;

during a second readout period after the first readout period, sequentially reading a second set of accumulated charge from the first row to the last row of the plurality of rows of pixels to produce a second set of imaging data; and generating one or more image frames based on the first set of imaging data and the second set of imaging data.

2. The method of claim 1, wherein transitioning the liquid crystal light shutter to the closed state to prevent the imager from receiving visible light comprises transitioning the liquid crystal light shutter to the closed state to prevent the imager from receiving ambient light.

3. The method of claim 1, wherein the imager is a rolling shutter imager and the visible-light illumination source is pulsed, the method further comprising:

illuminating the tissue of the subject with a primary visible-light illumination pulse of the pulsed visible-light illumination source while the liquid crystal light shutter is in the open state; and illuminating the tissue of the subject with one or more compensating visible-light illumination pulses of the pulsed visible-light illumination source after the primary visible-light illumination pulse of the pulsed visible-light illumination source and while the liquid crystal light shutter is in the closed state.

4. The method of claim 1, wherein the one or more image frames comprise a visible-light image frame based on the first set of imaging data and wherein the one or more image frames comprise a fluorescence image frame based on the second set of imaging data.

5. The method of claim 4, wherein the one or more image frames comprise a blended image frame based on the fluorescence image frame and the visible-light image frame.

6. The method of claim 5, wherein the fluorescence image frame is overlaid on the visible-light image frame in the blended image frame.

7. The method of claim 5, wherein the blended image frame is derived from colorizing the visible-light image frame based on the fluorescence image frame.

8. The method of claim 7, wherein the blended image frame is derived from colorizing the visible-light image frame based on the ratio of the fluorescence image frame to one or more channels of the visible-light frame.

9. The method of claim 1, further comprising: adding the one or more image frames to a video stream.

10. The method of claim 3, wherein the primary visible-light illumination pulse is a first primary visible-light illumination pulse, the method further comprising:

during the second readout period, transitioning the liquid crystal light shutter to the open state to allow illumination of the tissue of the subject with a second primary visible-light illumination pulse of the pulsed visible-light illumination source to accumulate charge at the plurality of rows of pixels of the imager, wherein the second primary visible-light illumination pulse is immediately after the one or more compensating visible-light illumination pulses.

11. The method of claim 3, wherein the first readout period and the second readout period form an image acquisition rotation, the method further comprising: performing one or more additional image acquisition rotations.

12. The method of claim 11, wherein the fluorescence excitation illumination source is continuously on during the image acquisition rotation.

13. The method of claim 11, wherein the fluorescence excitation illumination source is pulsed to reduce fluorescence intensity in the second set of imaging data.

14. The method of claim 11, wherein the fluorescence excitation illumination source is pulsed, and wherein the fluorescence excitation illumination source is configured to output a single fluorescence excitation illumination pulse during the image acquisition rotation to illuminate the tissue of the subject.

15. The method of claim 1, wherein the fluorescence excitation illumination source is pulsed, the method further comprising:

during a third readout period after the second readout period, sequentially reading a third set of accumulated charge at the plurality of rows of pixels from the first row to the last row of the plurality of rows to produce a third set of imaging data, wherein the pulsed fluorescence excitation illumination source is configured to output a single pulse spanning the second readout period during the first readout period, the second readout period, and the third readout period.

16. The method of claim 15, wherein the first readout period, the second readout period, and the third readout period form an image acquisition rotation, the method further comprising:

performing one or more additional image acquisition rotations.

17. The method of claim 15, wherein the one or more image frames comprise a visible-light image frame based on the first set of imaging data and wherein the one or more image frames comprise a fluorescence image frame based on the second set of imaging data and the third set of imaging data.

18. The method of claim 15, further comprising:

adding an ambient readout period between the first readout period and the second readout period; and during the ambient readout period, sequentially reading a fourth set of accumulated charge at the plurality of rows of pixels from the first row to the last row of the plurality of rows to produce a set of ambient imaging data.

19. The method of claim 18, wherein the first readout period, the ambient readout period, the second readout period, and the third readout period form an image acquisition rotation, the method further comprising:

performing one or more additional image acquisition rotations.

20. The method of claim 18, wherein the one or more image frames comprise a visible-light image frame based on the first set of imaging data and wherein the one or more image frames comprise a fluorescence image frame based on the second set of imaging data, the third set of imaging data, and the set of ambient imaging data.

21. The method of claim 1, further comprising: resetting the plurality of rows of pixels of the imager before illuminating the tissue of the subject with the primary visible-light illumination pulse of the pulsed visible-light illumination source.

22. The method of claim 21, wherein resetting the plurality of rows of pixels of the imager comprises triggering a synchronous frame reset functionality of the imager.

23. The method of claim 1, wherein the visible-light illumination source comprises an LED.

24. The method of claim 1, wherein the fluorescence excitation illumination source comprises an infrared light.

25. The method of claim 1, wherein the imager is part of an endoscopic imager.

26. The method of claim 1, wherein the imager comprises a CMOS sensor.

27. The method of claim 1, wherein the visible-light illumination source comprises a white-light illumination source.

28. A system of imaging tissue of a subject, the system comprising:

a fluorescence excitation illumination source, a visible-light illumination source, a liquid crystal light shutter configurable to be in an open state and a closed state, and an imager being configured for:

transitioning the liquid crystal light shutter to the open state to allow reflected light from illumination of the tissue of the subject with the visible-light illumination source to accumulate charge at a plurality of rows of pixels of the imager;

transitioning the liquid crystal light shutter to the closed state to prevent the imager from receiving visible light;

during a first readout period, sequentially reading a first set of accumulated charge at the plurality of rows of pixels from a first row to a last row of the plurality of rows to produce a first set of imaging data;

illuminating the tissue of the subject with the fluorescence excitation illumination source while the liquid crystal light shutter is in the closed state, wherein the visible light is blocked by the liquid crystal light shutter and light emitted due to illumination with the fluorescence excitation light source is passed through the liquid crystal light shutter;

during a second readout period after the first readout period, sequentially reading a second set of accumulated charge from the first row to the last row of the plurality of rows of pixels to produce a second set of imaging data; and generating one or more image frames based on the first set of imaging data and the second set of imaging data.

* * * * *